US012390250B2

(12) United States Patent
Roberts et al.

(10) Patent No.: US 12,390,250 B2
(45) Date of Patent: Aug. 19, 2025

(54) DEVICE FOR INDICATING AN ACTIVE COMPONENT OF AN ADJUSTABLE MEDICAL APPARATUS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Brian Roberts, Germantown, TN (US); Johnny R. Mason, Bartlett, TN (US); Paul Bell, Memphis, TN (US); Andrew P. Noblett, Bartlett, TN (US); Haden Janda, Germantown, TN (US); Charles C. Heotis, Germantown, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 348 days.

(21) Appl. No.: 18/009,962

(22) PCT Filed: Aug. 5, 2021

(86) PCT No.: PCT/US2021/044611
§ 371 (c)(1),
(2) Date: Dec. 12, 2022

(87) PCT Pub. No.: WO2022/031891
PCT Pub. Date: Feb. 10, 2022

(65) Prior Publication Data
US 2023/0233232 A1    Jul. 27, 2023

Related U.S. Application Data

(60) Provisional application No. 63/062,080, filed on Aug. 6, 2020.

(51) Int. Cl.
*A61B 17/66* (2006.01)
*A61B 17/00* (2006.01)
*A61B 90/00* (2016.01)

(52) U.S. Cl.
CPC .... *A61B 17/66* (2013.01); *A61B 2017/00477* (2013.01); *A61B 2090/0807* (2016.02)

(58) Field of Classification Search
CPC ......... A61B 17/62; A61B 17/64; A61B 17/66; A61B 5/48; A61B 5/4824; A61B 5/4833;
(Continued)

(56) References Cited

U.S. PATENT DOCUMENTS

| | | | |
|---|---|---|---|
| 2011/0004199 A1* | 1/2011 | Ross | A61B 90/98 606/1 |
| 2017/0071632 A1* | 3/2017 | Vikinsky | A61B 17/62 |
| 2019/0231259 A1* | 8/2019 | Cohen | A61B 5/4824 |

FOREIGN PATENT DOCUMENTS

| | | |
|---|---|---|
| WO | 2009105479 A1 | 8/2009 |
| WO | 2014186453 A2 | 11/2014 |

(Continued)

OTHER PUBLICATIONS

International Search Report and Written Opinion for the Application No. PCT/US2021/044611, mailed Nov. 19, 2021, 17 pages.

*Primary Examiner* — Christopher J Beccia
(74) *Attorney, Agent, or Firm* — KDW Firm PLLC

(57) ABSTRACT

An adjustment compliance device and systems and methods for use with an external fixator are disclosed. The adjustment compliance device can be attached to a strut of an external fixator and may include at least one indicator element to indicate adjustment parameters for an active step of an adjustment process for the external fixator. The adjustment parameters may include an active strut and/or a direction of adjustment for the strut. The adjustment compliance device may receive the adjustment parameters from a user device.

(Continued)

The at least one indicator element may include a light element operative to emit light in a color corresponding to the active strut. The at least one indicator element may include a light element configured to indicate a direction of rotation of the active strut. As a result, a patient can more effectively comply with an adjustment prescription, thereby improving the likelihood of successful bone alignment.

3 Claims, 29 Drawing Sheets

(58) Field of Classification Search
CPC ........... A61B 5/11; A61B 5/1121; A61B 5/72; A61B 5/7246
See application file for complete search history.

(56) References Cited

FOREIGN PATENT DOCUMENTS

| WO | 2015136544 | A1 | 9/2015 |
| WO | 2020160076 | A1 | 8/2020 |

* cited by examiner

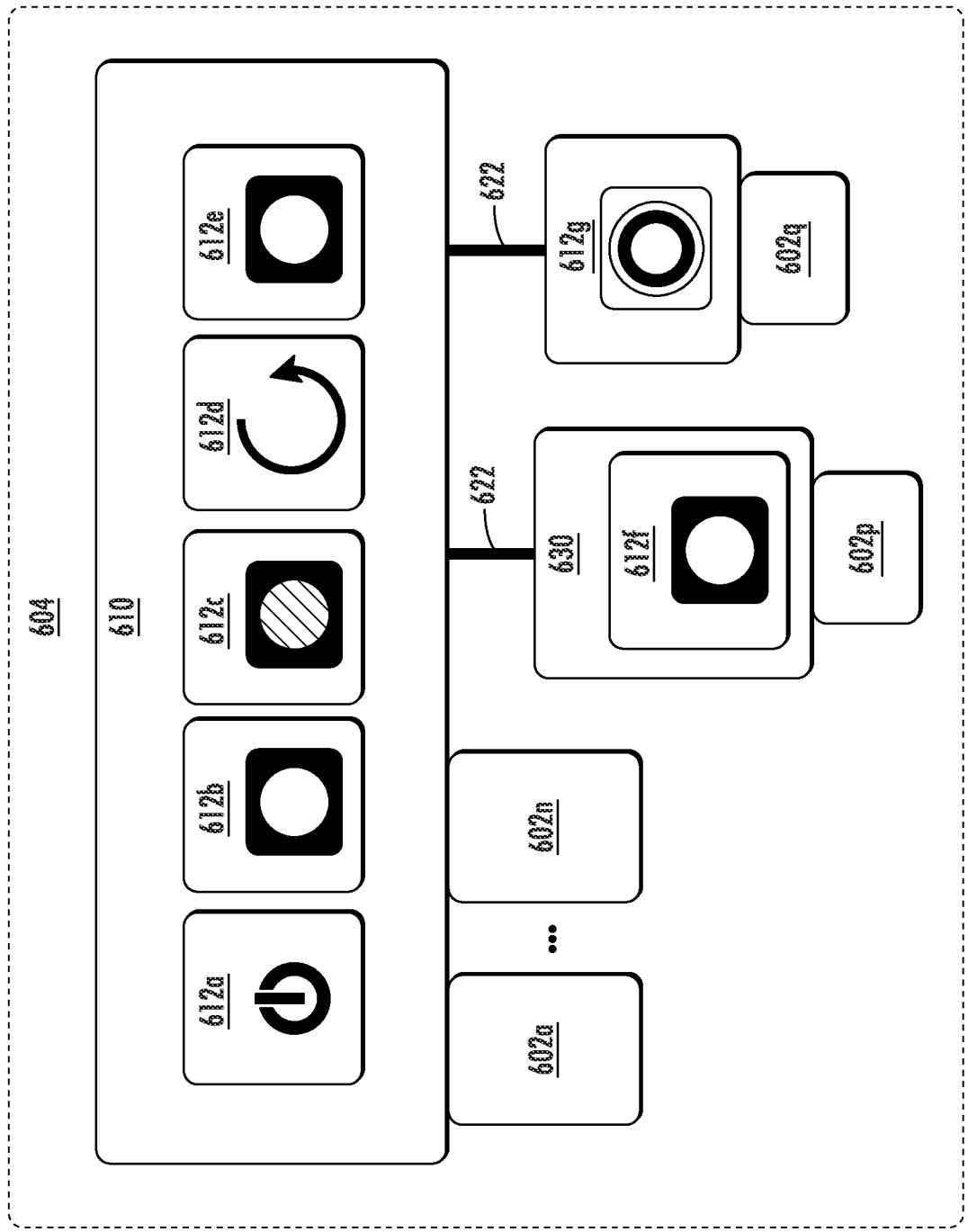

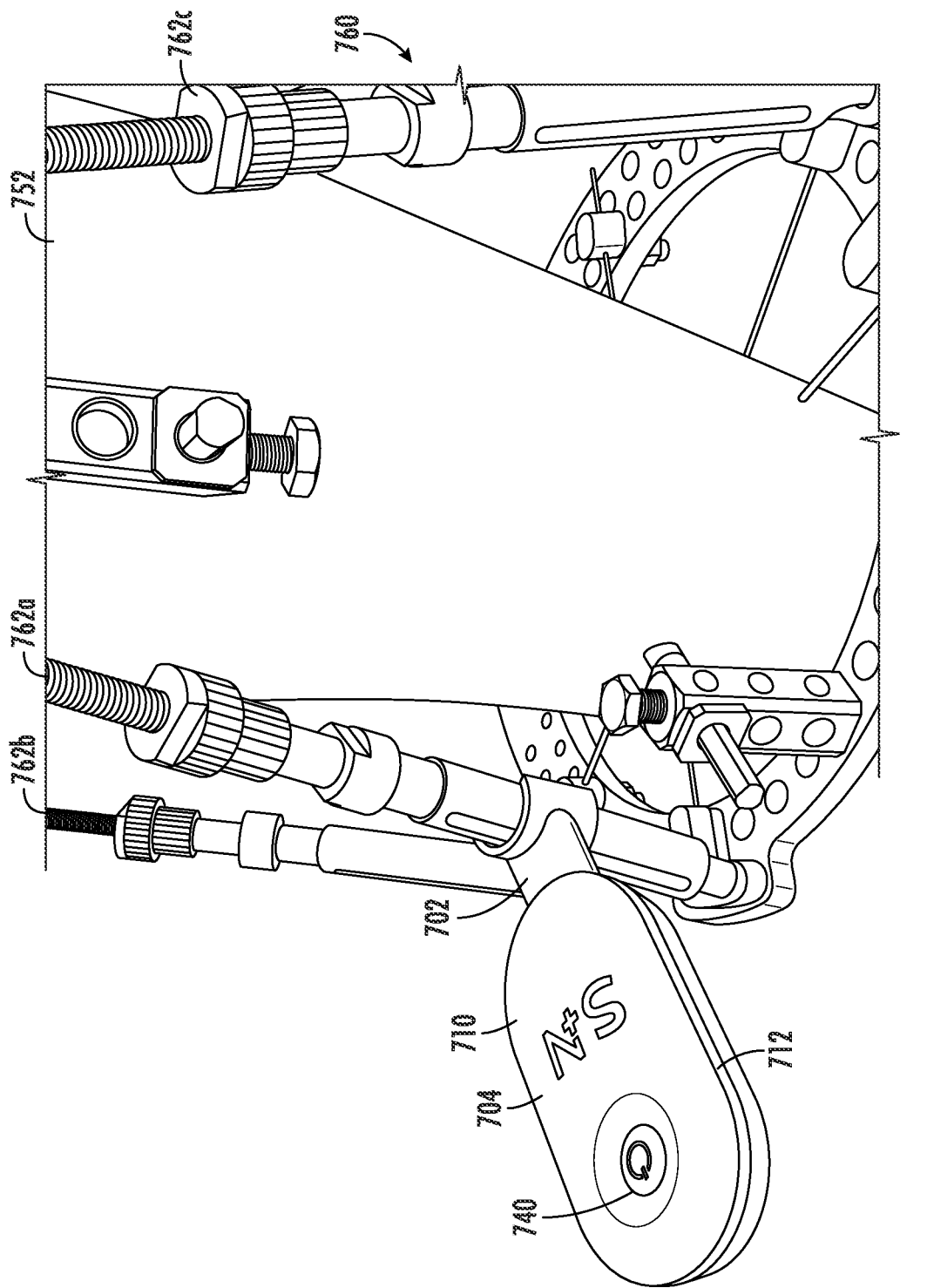

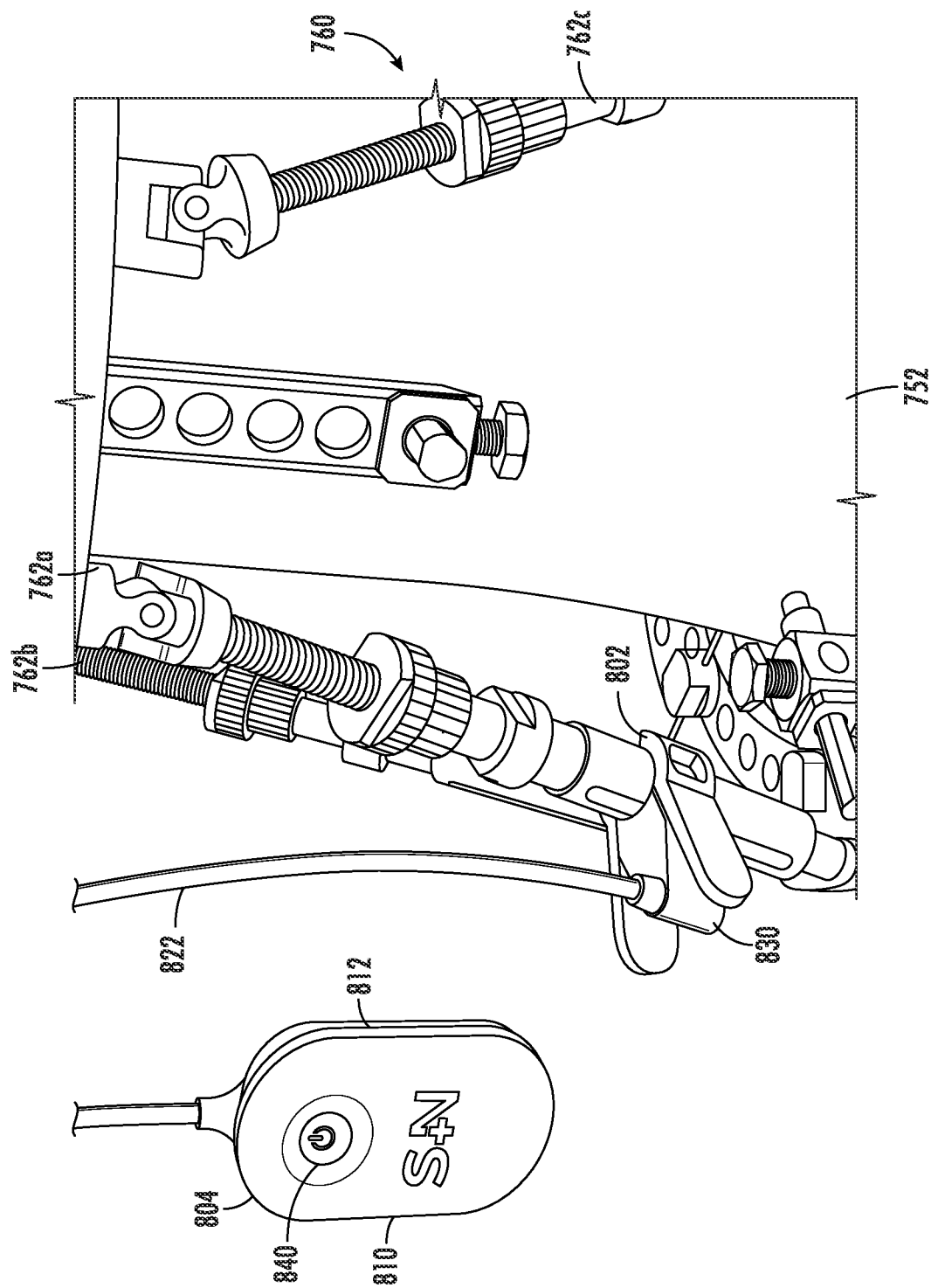

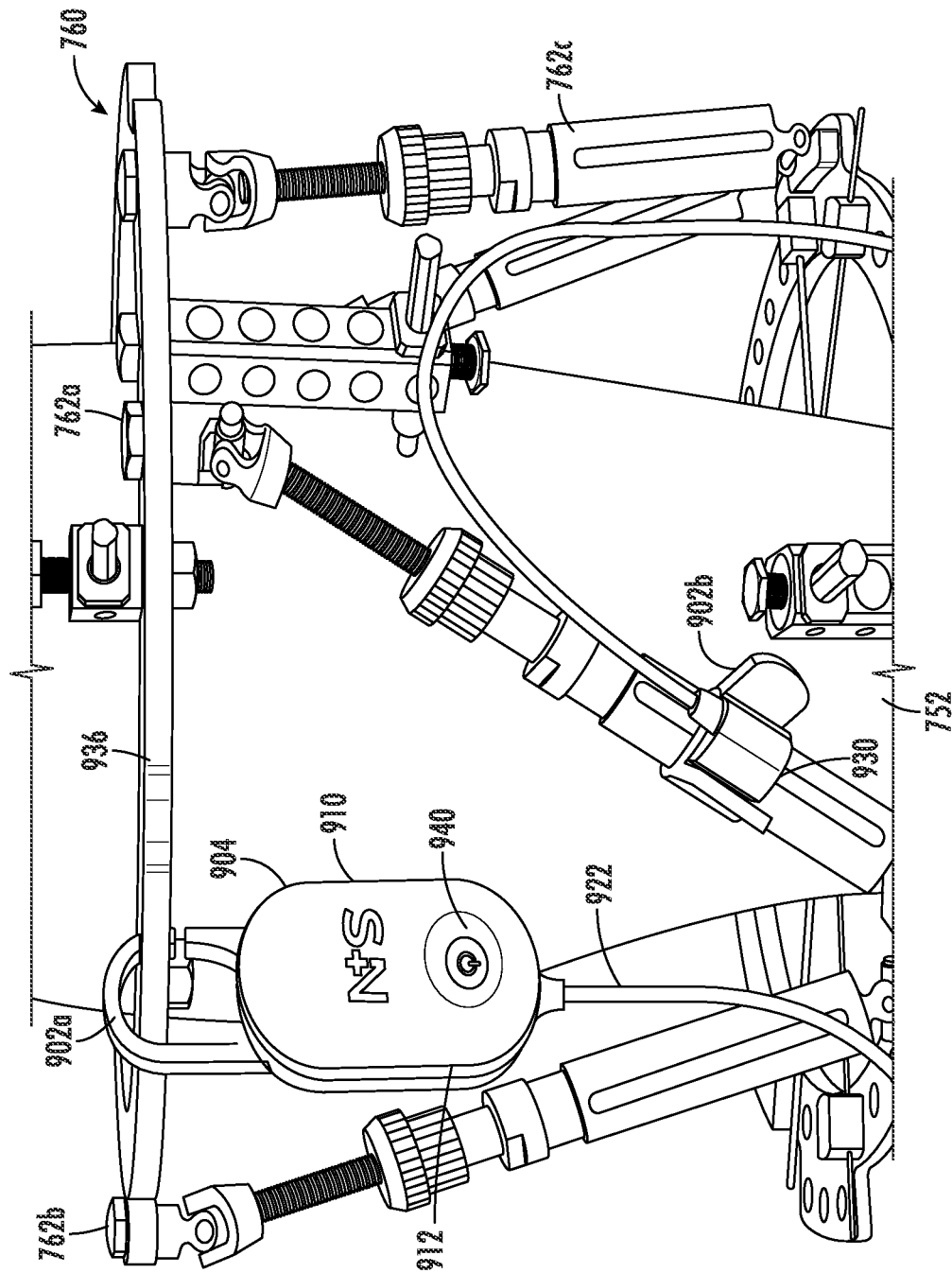

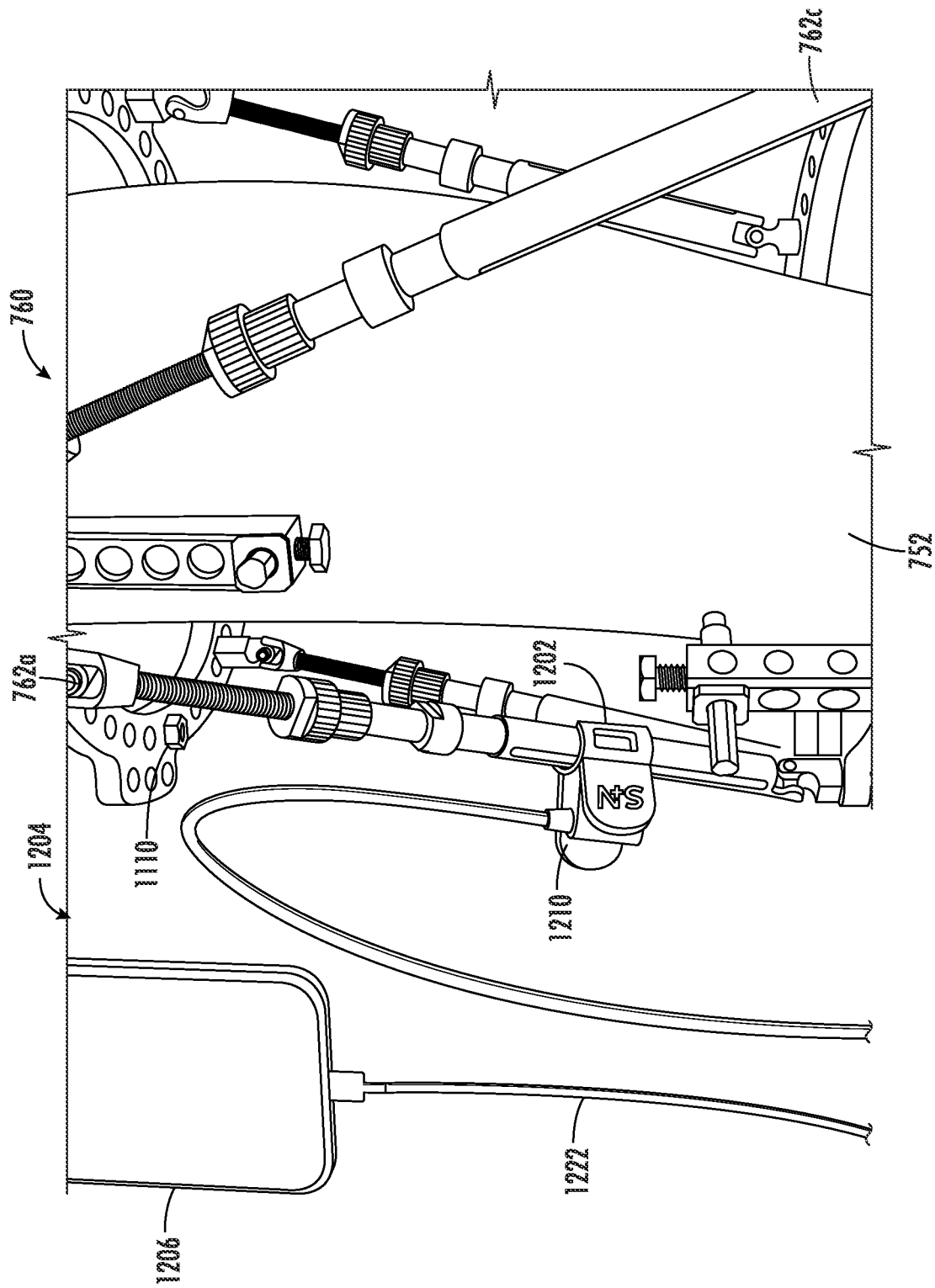

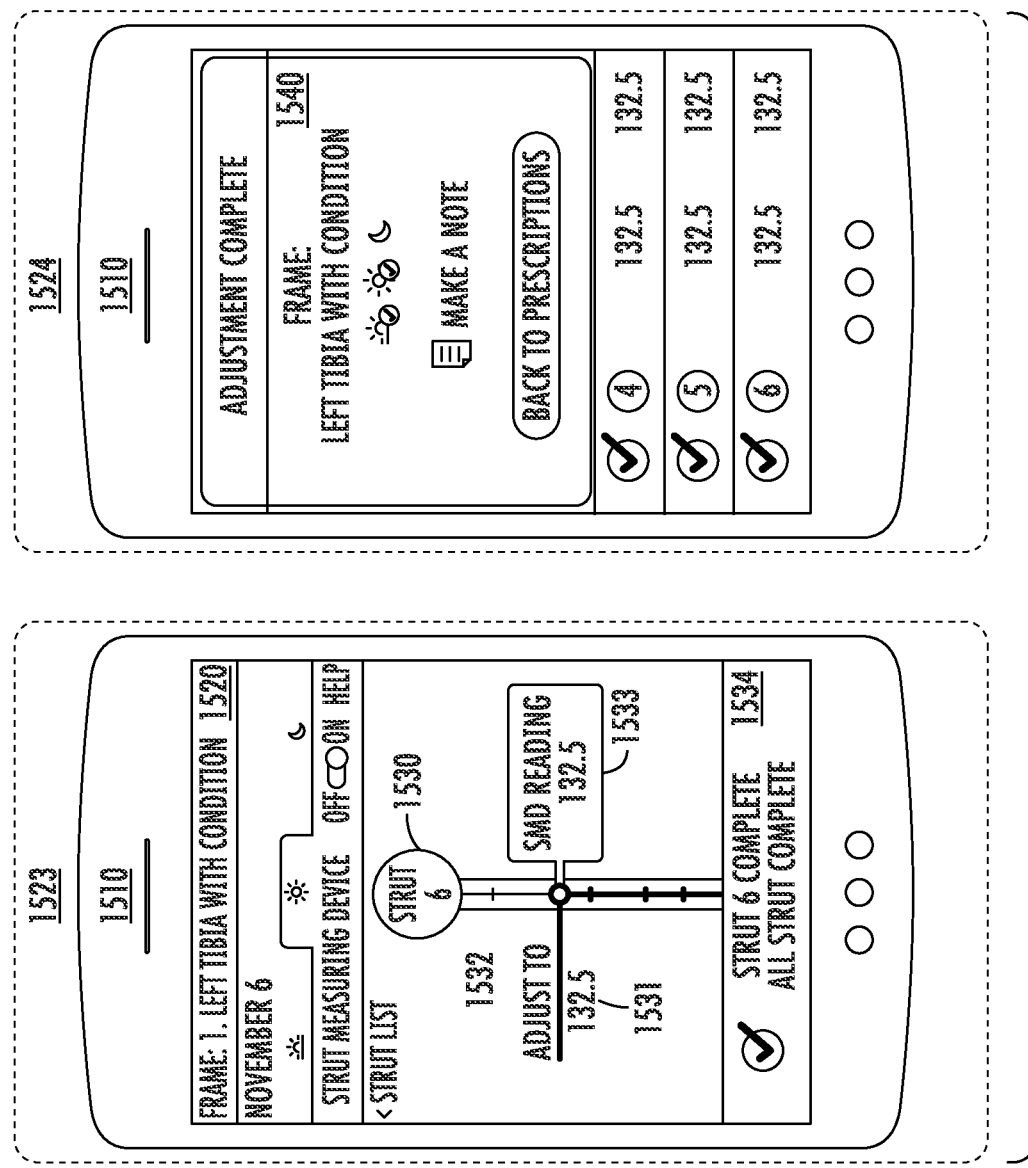

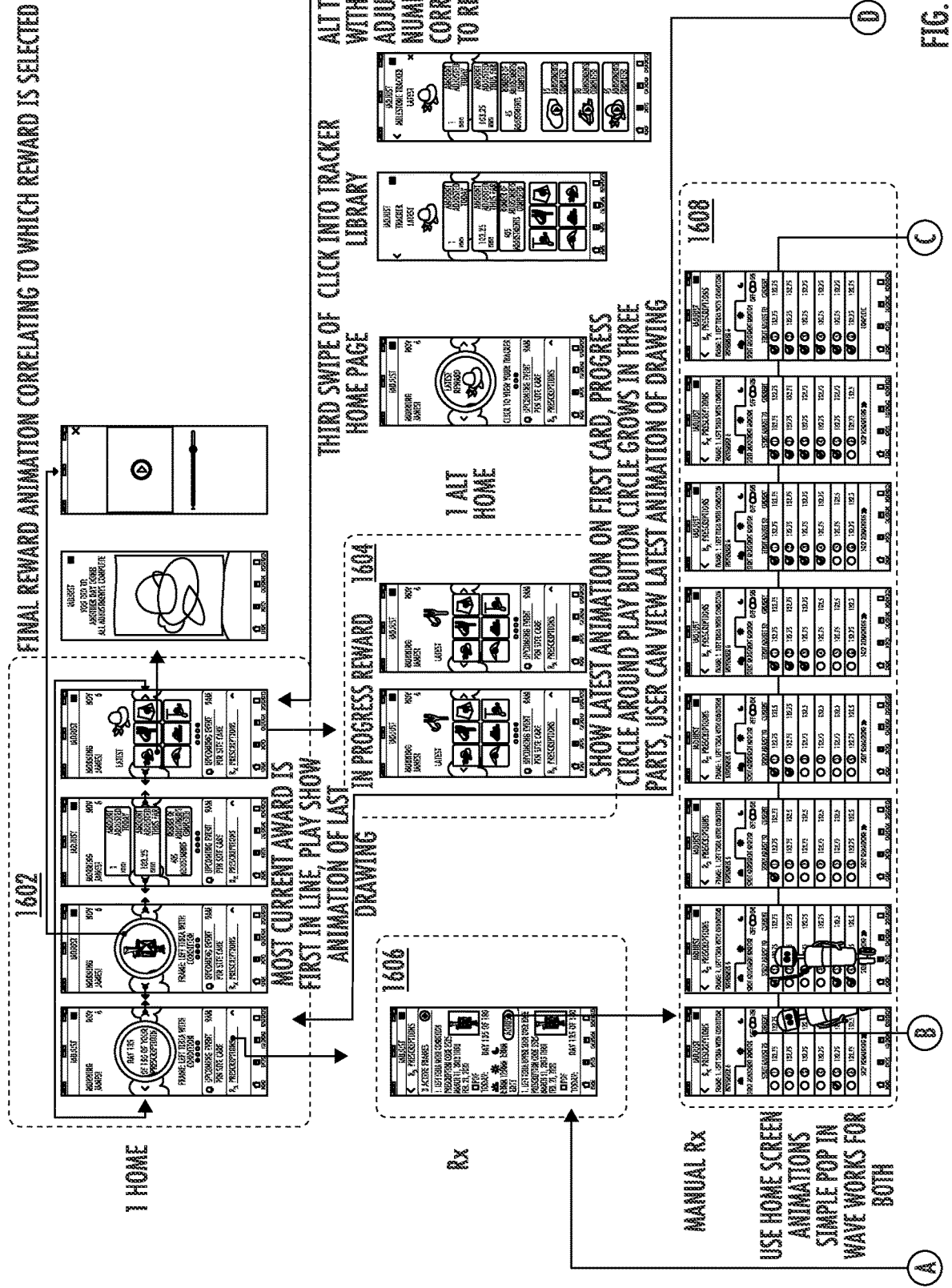

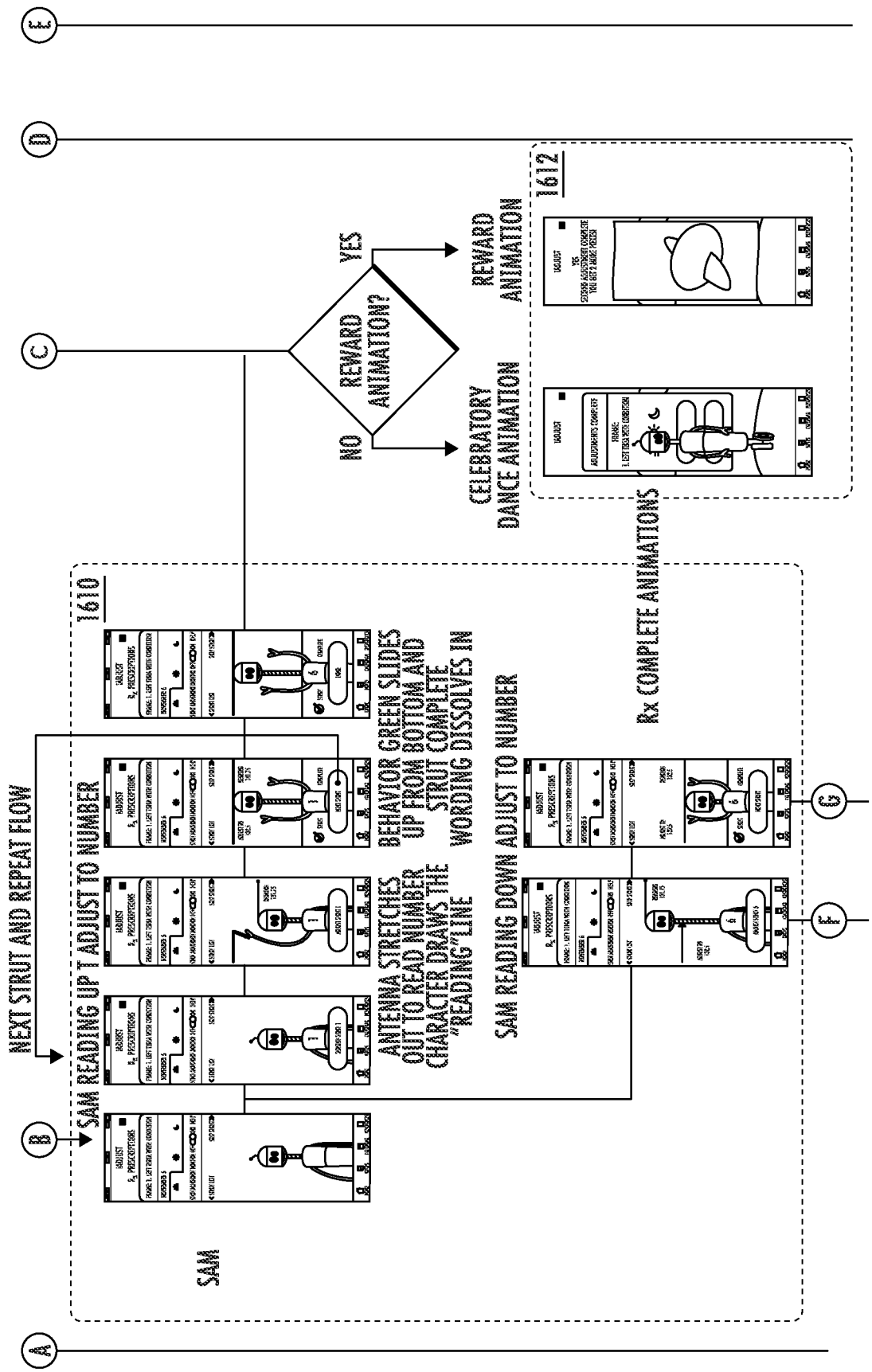

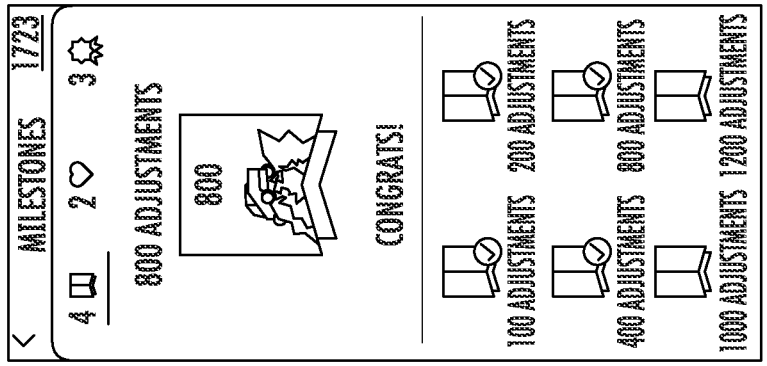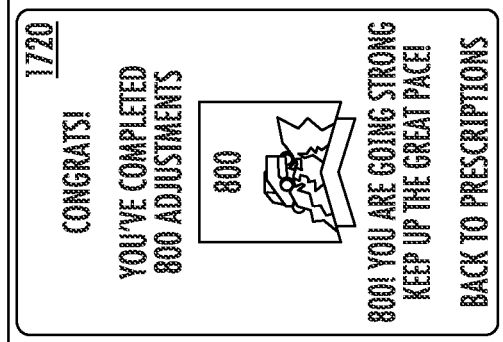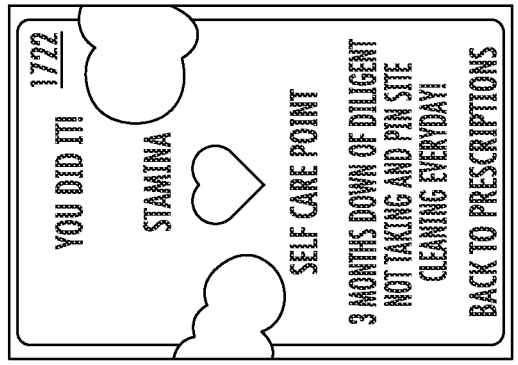
FIG. 17

DEVICE FOR INDICATING AN ACTIVE COMPONENT OF AN ADJUSTABLE MEDICAL APPARATUS

CROSS-REFERENCE TO RELATED APPLICATION

This application is a National Phase filing of International Application No. PCT/US2021/044611, filed Aug. 5, 2021, which application claims the benefit of U.S. Provisional Patent Application Ser. No. 63/062,080, filed Aug. 6, 2020, and titled "Device for Indicating an Active Component of an Adjustable Medical Apparatus," the entire contents of each application is hereby incorporated by reference in its entirety.

FIELD OF THE DISCLOSURE

The present disclosure relates generally to orthopedic devices, systems, and methods for facilitating fracture alignment, and particularly to a device for use with an external fixator to provide a real-time indicator of an active strut to be adjusted to ensure that length adjustments are made in accordance with a predetermined prescription.

BACKGROUND OF THE DISCLOSURE

A patient that suffers a bone fracture may be required to use a bone alignment device, or external fixator, to align two or more bones or pieces of bone. The bone alignment device often has multiple struts that are to be adjusted regularly (e.g., daily) in accordance with a prescription. The prescription specifies strut length adjustments to be made over time to ensure successful bone alignment.

Typically, the patient or a health care professional manually adjusts the struts of the bone alignment device. The strut adjustment process is a challenging and error-prone process that is difficult for patients to carry out properly. For example, individuals often adjust the incorrect strut and/or adjust the strut to an incorrect length. Adjustments to the struts that do not comply with the prescription can cause significant setbacks to the care of the patient.

Thus, it would be beneficial to provide an easy to use apparatus, system, and method that confirms that adjustments are being made to the correct strut. The present disclosure addresses this need.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides an adjustment compliance device. The adjustment compliance device may be attached to a strut of an external fixator. In an embodiment, the adjustment compliance device may include at least one indicator element to indicate adjustment information for an adjustment process. In exemplary embodiments, the adjustment process may include a process for adjusting struts of an external fixator device according to a hardware adjustment prescription. The prescription may be generated by the patient's surgeon, for example, from surgeon-facing software. The prescription can then be loaded into the adjustment compliance device.

In one embodiment, an adjustment compliance device for an adjustable medical apparatus may include a main body having a coupling element to couple the adjustment compliance device to a portion of the adjustable medical apparatus, a communication interface for communicatively coupling the adjustment compliance device to an external computing device, a logic device configured to receive indicator information from the external computing device, and at least one indicator element arranged on the main body, the logic device to control the at least one indicator element based on the indicator information to indicate at least one adjustment parameter for adjustment of the adjustable medical apparatus according to an adjustment prescription.

In one embodiment, a method for facilitating compliance with an adjustable medical apparatus adjustment process may include attaching an adjustment compliance device to a portion of the adjustable medical apparatus, the adjustment compliance device communicatively coupled to a computing device, generating indicator information via the computing device based on an adjustment prescription, transmitting, via the computing device, the indicator information to the adjustment compliance device, controlling, via the adjustment compliance device, at least one indicator element arranged on the adjustment compliance device based on the indicator information to indicate at least one adjustment parameter for adjustment of the adjustable medical apparatus according to an adjustment prescription.

In some embodiments, the at least one indicator element may include a light element operative to be activated to present indicator information. In some embodiments, indicator information may include adjustment parameters for a current step of the adjustment process. In various embodiments, the adjustment parameters may include an active component. In some embodiments, the active component may include a next strut to be adjusted for the adjustment process. In exemplary embodiments, the light element may be activated to emit a light corresponding to a color associated with the active component. In some embodiments, the light element may include a light emitting diode (LED) light element configured to emit a plurality of colors of light.

In some embodiments, the adjustment parameters may include a direction indicator configured to indicate a direction to adjust the active component. In exemplary embodiments, the direction indicator may indicate that the active component needs to be rotated one of clockwise or counterclockwise. In various embodiments, the direction indicator may indicate that the active component needs to be adjusted via one of lengthening or shortening of the active component. In some embodiments, the at least one indicator element may include a direction light element operative to indicate the adjustment parameters. In exemplary embodiments, the direction light element may be configured to indicate a direction of rotation of the active component.

In exemplary embodiments, the at least one indicator element may include a series of light elements. In some embodiments, the series of light elements may include a light element for each of the struts of an external fixator.

In various embodiments, the at least one indicator element may include an audio element configured to provide the adjustment parameters via audio signals. In some embodiments, the at least one indicator element may include graphical indicator configured to provide the adjustment parameters via graphical signals. In various embodiments, the graphical indicator may include a screen operative to display graphical and/or textual information. In exemplary embodiments, the at least one indicator element may include a tactile or haptic element configured to provide tactile-based or haptic-based adjustment parameters.

In some embodiments, the adjustment compliance device may be or may include a strut measurement and feedback device operative to confirm that the strut measurement and feedback device is attached to a proper strut to be adjusted. The strut measurement and feedback device can determine if a length adjustment to the strut is correct. The strut measurement and feedback device can provide real-time feedback to an individual as the length of the strut is being adjusted to ensure the length adjustment complies with a prescription for the length of the strut. As a result, a patient can more effectively comply with the prescription as adjustments to the strut are made over time, thereby improving the likelihood of successful bone alignment.

In one embodiment, the adjustment compliance device can include a coupling component, at least one indicator element, and a communications interface. In some embodiments, the adjustment compliance device may also include a strut measurement component. The coupling component enables the adjustment compliance device to be selectively attached and detached from a strut of an external fixator. The strut measurement component can determine which particular strut the adjustment compliance device is attached to. The strut measurement component can also determine an absolute or relative positioning or length of a strut to which the strut measurement and feedback device is attached. The communications interface can provide measurement data and identification data regarding the strut to a user device to provide real-time feedback regarding adjustments to the length of the strut to an individual making the adjustments. The communications interface may allow adjustment compliance device to receive indicator information from a user device to operate indicator elements to present indicator information.

In one embodiment, the strut measurement component can include a camera for visualizing markings on the strut that can be used to determine the motion, position, or length of the strut.

In one embodiment, the strut measurement component can include a scanner for reading a barcode of the strut to identify the strut.

In one embodiment, the strut measurement component can include a radio-frequency identification (RFID) scanner for reading an RFID tag of the strut to identify the strut.

In one embodiment, the communications interface component can include a wireless communications interface for transmitting the measurement data and the identification data regarding the strut to the user device. In one embodiment, the wireless communications interface may be used for receiving indicator information from the user device.

In one embodiment, the strut measurement and feedback device may include a device to adjust a length of the strut to which the strut measurement and feedback device is attached.

In one embodiment, the device for adjusting the length of the strut is configured to be removably attached to the strut measurement and feedback device.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 6 illustrates a block diagram of an embodiment of an adjustment compliance device;

FIGS. 7A and 7B illustrate a first embodiment of an adjustment compliance device;

FIGS. 8A and 8B illustrate a second embodiment of an adjustment compliance device;

FIGS. 9A and 9B illustrate a third embodiment of an adjustment compliance device;

FIGS. 12A and 12B illustrate a sixth embodiment of an adjustment compliance device;

FIGS. 15A and 15B illustrate a computing device depicting embodiments of an external fixator adjustment screen;

FIGS. 16A-16C illustrate screens of an embodiment of an external fixator adjustment application;

FIG. 17 illustrate embodiments of external fixator adjustment incentive screens.

Figure 1:
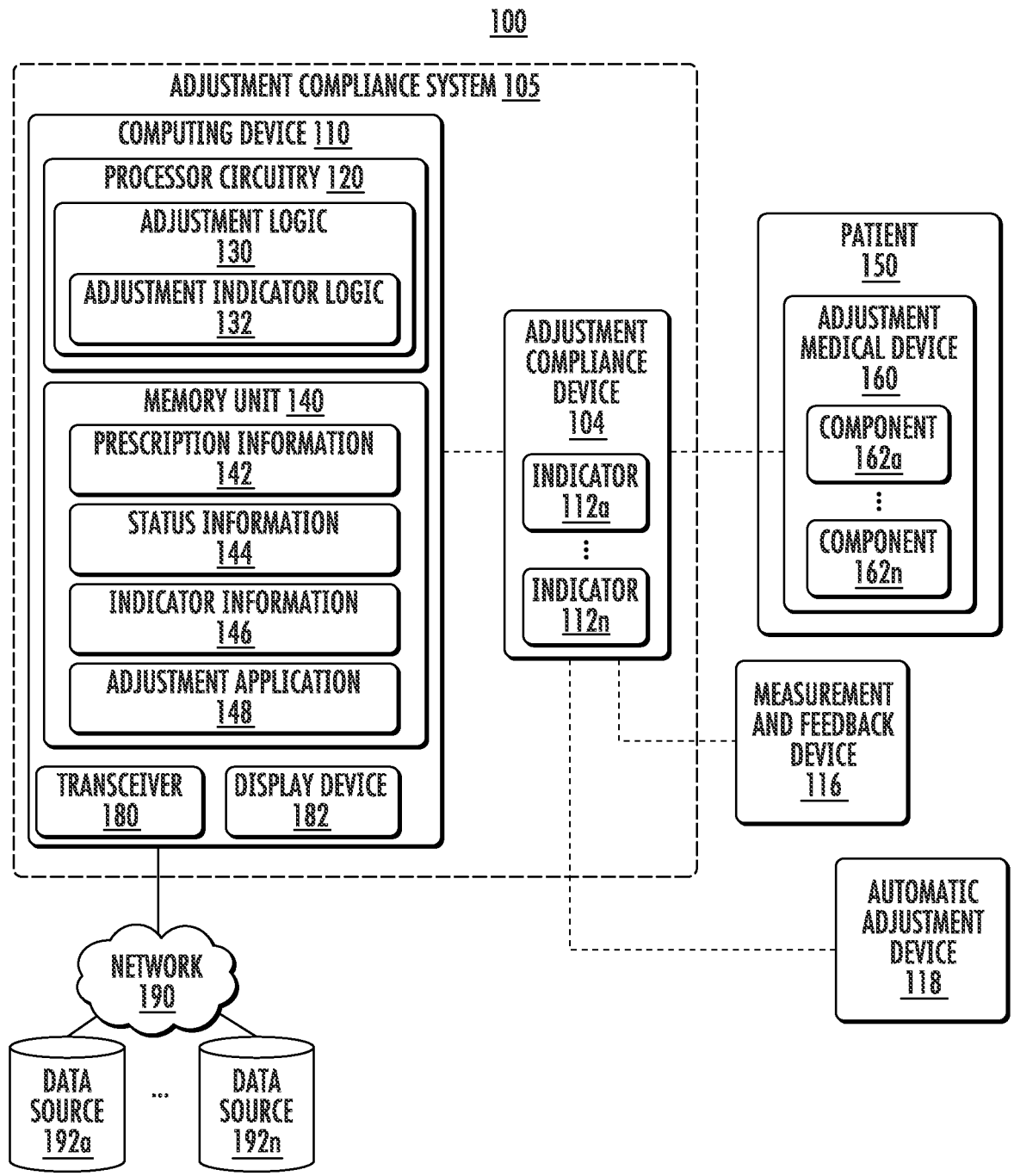
FIG. 1 depicts an example of a first operating environment that may be representative of some embodiments of the present disclosure.

The drawings are not necessarily to scale. The drawings are merely representations, not intended to portray specific parameters of the disclosure. The drawings are intended to depict various embodiments of the disclosure, and therefore are not be considered as limiting in scope. In the drawings, like numbering represents like elements.

DETAILED DESCRIPTION

For the purposes of promoting an understanding of the principles of the present disclosure, reference will now be made to the embodiments illustrated in the figures and specific language will be used to describe the same. It will nevertheless be understood that no limitation of the scope of the disclosure is thereby intended. Any alterations and further modifications in the described embodiments, and any further applications of the principles of the present disclosure as described herein are contemplated as would normally occur to one skilled in the art to which the disclosure relates.

Various features of an adjustment compliance system and method will now be described more fully hereinafter with reference to the accompanying drawings, in which one or more features of the adjustment compliance system and/or method will be shown and described. It should be appreciated that the various features may be used independently of, or in combination, with each other. It will be appreciated that the adjustment compliance system and method as disclosed herein may be embodied in many different forms and should not be construed as being limited to the embodiments set forth herein. Rather, these embodiments are provided so that this disclosure will convey certain illustrations of features of the healing status analysis system and method to those skilled in the art The present disclosure relates generally to an adjustment compliance system configured to provide adjustment information for an individual to adjust components of an adjustable medical apparatus, for example, according to a prescription. In some embodiments, the adjustable medical apparatus may be or may include a bone alignment device, such as an external fixator. In various embodiments, the external fixator may be the same or substantially similar to a Taylor Spatial Frame™ manufactured and sold by Smith & Nephew, Inc. of Cordova, Tennessee, United States. In various embodiments, an adjustment compliance system may include an adjustment compliance device configured to provide signals or other indicators to specify which component of an adjustable medical device is active. In general, the active component is the component that is currently specified for adjustment, for example, according to a prescription. In general, the prescription may be generated by a surgeon, for example, from surgeon-facing software. The generated prescription may be input into the adjustment compliance system.

For example, in some embodiments, the adjustment compliance device may include lights or other elements that may be capable of being controlled to indicate which strut of an external fixator device is currently specified for adjustment. An external fixator, such as a Taylor Spatial Frame™ may have a plurality of struts that require adjustment according to a prescription. Each strut may have a color-coded identification band, each with a unique color and number (for instance, strut 1 is "red," strut 2 is "orange," strut 3 is "yellow," strut 4 is "green," strut 5 is "blue," and strut 6 is "purple"). The adjustment compliance device may be configured to control an indicator light to light up in a color corresponding to the active strut. For instance, if a prescription provides that strut 3 is next for adjustment, a light on the adjustment compliance device may light up yellow to correspond with strut 3. Indicator elements may be activated in response to an action, timed event, or sequence of event(s) of the adjustment compliance device or adjustment compliance system. As described below, an adjustment compliance device may include other indicator elements, for example, a directionality indicator configured to indicate the direction of rotation for the active strut. Embodiments are not limited in this context.

FIG. 1 illustrates an example of an operating environment 100 that may be representative of some embodiments. As shown in FIG. 1, operating environment 100 may include an adjustment compliance system 105. In various embodiments, adjustment compliance system 105 may include a computing device 110 that, in some embodiments, may be communicatively coupled to network 190 via a transceiver 180. Computing device 110 may be or may include one or more logic devices, including, without limitation, a server computer, a client computing device, a personal computer (PC), a workstation, a laptop, a notebook computer, a smart phone, a tablet computing device, and/or the like. Embodiments are not limited in this context.

As shown in FIG. 1, adjustment compliance system 105 may include or may be communicatively coupled to an adjustment compliance device 104. In some embodiments, computing device 110 may be a smart phone or other mobile computing form factor in wired or wireless communication with adjustment compliance device 104. For example, computing device 110 and adjustment compliance device may communicate via various wireless protocols, including, without limitation, Wi-Fi (i.e., IEEE 802.11), radio frequency (RF), Bluetooth™, Zigbee™, near field communication (NFC), Medical Implantable Communications Service (MICS), and/or the like. In another example, computing device 110 and adjustment compliance device may communicate via various wired protocols, including, without limitation, universal serial bus (USB), Lightning, serial, and/or the like. Although computing device 110 (and components thereof) and adjustment compliance device 104 are depicted as separate devices, embodiments are not so limited. For example, in some embodiments, computing device 110 and adjustment compliance device 104 may be a single device. In another example, some or all of the components of computing device 110 may be included in adjustment compliance device 104.

Figure 2:
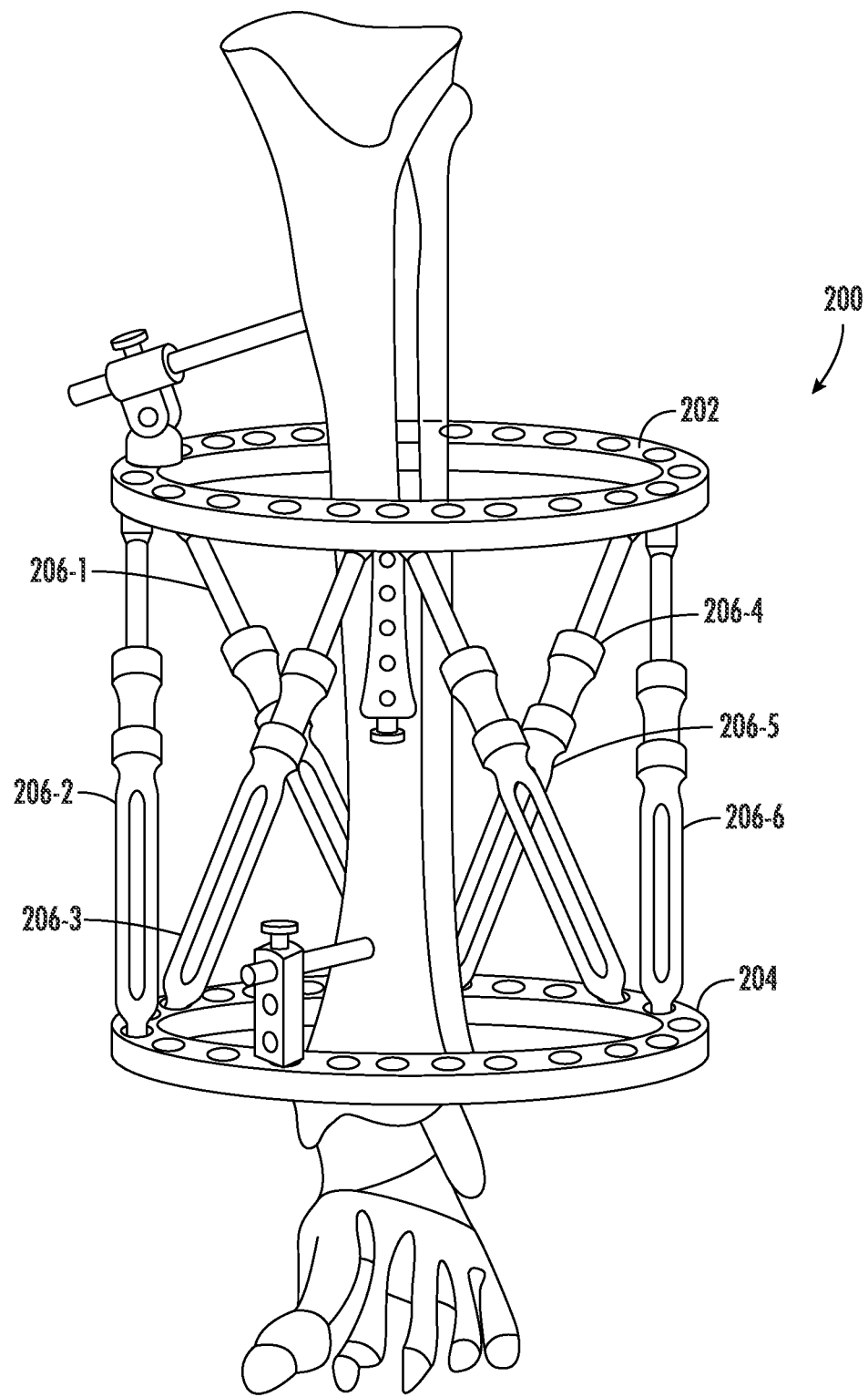
FIG. 2 illustrates an embodiment of a bone alignment device.

As shown in FIG. 1, a patient 150 may be associated with an adjustable medical device 160, such as a bone alignment device or external fixator device having a plurality of components 162a-n (e.g., struts) at least a portion of which may require adjustment. FIG. 2 illustrates an embodiment of a bone alignment device 200. In some embodiments, adjustable medical device 160 may be the same or substantially similar to bone alignment device 200. As shown in FIG. 2, bone alignment device 200 can be an external fixator. Bone alignment device 200 can include a first bone coupling mechanism, member, device, etc., a second bone coupling mechanism, member, device, etc., and a plurality of interconnected telescopic struts. For example, as shown in FIG. 2, in one embodiment, bone alignment device 200 can form a hexapod having a circular, metal frame with a first ring 202 and a second ring 204 connected by six telescopic struts 206 (labeled as struts 206-1 through 206-6 in FIG. 2). Each strut 206 can be independently lengthened or shortened relative to the rest of the frame, thereby allowing for six different axes of movement.

In one embodiment, each strut 206 may include an outer body component and an inner rod component (e.g., a threaded rod). To lengthen or shorten one of struts 206, the outer body component and the inner rod component can be moved or translated relative to one another. Thus arranged, each strut may be in the form of a telescopic device. Often a strut pin coupled to the inner rod component can be visualized within a slot or opening formed in the outer body component to determine the relative movement of the inner rod component relative to the outer body component. For example, as the inner rod component is translated relative to the outer body component, the strut pin moves in unison with the inner rod component within the slot of the outer body component.

As will be described herein, the features according to the present disclosure may be used with any suitable bone alignment device now known or hereafter developed. In this regard, the present disclosure should not be limited to the details of the bone alignment device and/or struts disclosed and illustrated herein (for example, in FIG. 2) unless specifically claimed and that any suitable bone alignment device can be used in connection with the principles of the present disclosure.

Bone alignment device 200 can be used to treat a variety of skeletal fractures of a patient. Typically, bone alignment device 200 is positioned around the patient and is used to align two or more bones or pieces of bone. To do so, a length of each strut 206 can be incrementally adjusted (e.g., shortened or lengthened) in accordance with a prescription that specifies adjustments to be made to each strut 206 over time to ensure successful bone alignment. In many instances, the length of each strut 206 should be adjusted daily to comply with the provided prescription. As such, in use, a prescription may, for example, designate a specific amount of adjustment that needs to be made to each strut on, for example, a daily basis. In use, each strut may be adjusted daily by a varying amount.

In a manual adjustment process, adjustments to struts 206 are usually made directly by either the patient or a caregiver. To make an adjustment, an individual can refer to a graduated scale that is laser etched onto each strut 206. The scale, however, can be difficult for the individual making the adjustments to observe when bone alignment device 200 is positioned on the patient. In addition, it is challenging to determine the designator (e.g., strut number and/or color) to identify the correct active strut. To make an adjustment, the individual making the adjustment may also rely on a tactile "click" that can be felt by the patient when the length of the strut 206 is adjusted by a fixed amount (e.g., 1 mm). The tactile click, however, does not indicate the direction in which the strut 206 was adjusted. In addition, individuals may often adjust the incorrect strut (e.g., on a daily basis, each strut may need to be adjusted a different amount, the individual may inadvertently adjust the wrong strut, or adjust the correct strut by an incorrect amount). Furthermore, an individual may inadvertently rotate one or more struts in the wrong direction thereby, for example, shortening a strut instead of lengthening the strut. Thus, despite implementing safeguards such as, for example, the inclusion of the scale, tactile click, and color labels, it may be difficult for individuals to confirm that the proper strut is being adjusted and/or that the proper length of each strut 206 was reached as specified by the prescription when an adjustment to each strut 206 is made. As a result, it is common for individuals to not comply with the prescription when an adjustment is made.

A patient generally has follow-up clinical visits, for example, a patient may have a clinical visit every two weeks, so that the patient's clinician can evaluate the patient's progress and modify bone alignment device 200 or related prescription as necessary. Incorrect adjustments to struts 206 that can occur between clinical visits can result in significant deviations in the correction path of the bone fragments compared to what was prescribed, thereby causing significant setbacks in the treatment of the patient.

Referring to FIG. 1, adjustment compliance device 104 may include one or more indicators 112a-n operative to indicate an active component 162a-n (e.g., the next strut to adjust according to a prescription). In various embodiments, indicators 112a-n may be configured to signal other information in addition to or in the alternative of an active component 162a-n, such as a direction of rotation of an active strut. Indicators 112a-n may include various elements capable of proving information to a user, including, without limitation, lights, graphical user interface (GUI) device, audio devices, haptic devices, and/or the like.

For example, indicator 112a may be or may include a light or set of lights capable of being activated to present different colors. For instance, indicator 112a may include one or more light emitting diode (LED) lights capable of emitting light in colors corresponding to the designated strut colors. In some embodiments, lights may include incandescent light elements, gas-discharge light elements, halogen light elements, CFL light elements, or other light elements now known or developed in the future.

For example, if strut 1 is active, indicator 112a may emit red light. In another example, indicator 112n may be configured to indicate a directionality of rotation of strut 1 (for instance, based on prescription information 142 and/or status information 144 as described below). For example, indicator 112n may be configured to present an arrow, rotating light or graphic, and/or other signal to indicate a direction of rotating a strut. Accordingly, in one embodiment, if a prescription specifies that a current step requires adjusting strut 1 such that strut 1 requires clockwise rotation, indicator 112a may emit red light and indicator 112n may indicate clockwise rotation. As described in more detail in the present disclosure, indicators 112a-n may include various other types of signal elements associated with various other indicator information 146.

Computing device 110 may include a processor circuitry 120 that may include and/or may access various logics for performing processes according to some embodiments. For instance, processor circuitry 120 may include and/or may access an adjustment logic 130 and/or an adjustment indicator logic 132. Processing circuitry 120, adjustment logic 130 and/or adjustment indicator logic 132, and/or portions thereof may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, a proportional-integral-derivative (PID) controller, FG circuitry, variations thereof, combinations of any of the foregoing, and/or the like.

Although adjustment logic 132 is depicted in FIG. 1 as being within processor circuitry 120, embodiments are not so limited. For example, adjustment logic 130, adjustment indicator logic 132, and/or any component thereof may be located within an accelerator, a processor core, an interface, an individual processor die, implemented entirely as a software application (for instance, an adjustment application 148) and/or the like.

Memory unit 140 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 140 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 140 may store various types of information and/or applications for an adjustment compliance process according to some embodiments. For example, memory unit 140 may store prescription information 142, status information 144, indicator information 146, and/or an adjustment application 148. In some embodiments, prescription information 142, status information 144, indicator information 146, adjustment application 148, and/or portions thereof, may be stored in one or more data stores 192a-n accessible to computing device 110 via network 190.

In some embodiments, adjustment application 148 may be or may include an application being executed on computing device 110 (including a mobile application or "app" executing on a mobile device form factor). In various embodiments, adjustment application 148 may be or may include an application the same or similar to the iADJUST™ platform provided by Smith & Nephew, Inc. of Cordova, Tennessee, United States.

In some embodiments, prescription information 142 may include a prescription for adjusting adjustable medical device 160. For example, a prescription may specify adjustment of components 162a-n based on a schedule (for instance, on day X, strut 1 should have a length of (or should be moved in a specified direction a distance) Y, strut 2 should have a length of (or should be moved in a specified direction a distance) Z, and so on). Status information 144 may include a status of components 162a-n, such as the active component (e.g., next component requiring adjustment), current positions (e.g., length), last rotation direction, and/or the like. For example, status information 144 may include the current length of each strut.

In various embodiments, indicator information 146 may include information that may be used to facilitate compliance for adjusting components 162a-n. For example, indicator information 146 may include the active component 162a-n (i.e., the next strut to be adjusted), adjustment directionality, adjustment amount, and/or the like. For example, a prescription may specify that strut 1 is supposed to be moved to position X. Adjustment application 148 may access status information 144 to determine the current position of strut 1 to determine the required direction of rotation (for instance, clockwise to lengthen and counter-clockwise to shorten, or vice versa). The active strut (i.e., strut 1) and/or the directionality may be specified as indicator information 146 provided to adjustment compliance device 104 to provide an indication of the active component 162a-n and other adjustment parameters (e.g., a direction to rotate an active strut) to a user.

In some embodiments, as described in more detail below, adjustment compliance system may include a measurement and feedback device 116. In various embodiments, measurement and feedback device 116 can be coupled to each strut one at a time. In use, in one embodiment, the strut measurement and feedback device 116 can determine which strut the strut measurement and feedback device 116 is coupled to and can provide real-time feedback as to the position of each strut (e.g., can determine absolute position of each strut, which can then be used to determine the change in length which the strut undergoes by, for example, comparing the start position to the finish position). A non-limiting example of a measurement and feedback device is described in International Application No. PCT/US2020/015558, entitled "Device for External Fixation Strut Measurement and Real-Time Feedback," which is incorporated by reference as if fully set forth in the present disclosure.

Use of measurement and feedback device 116 requires that a user place measurement and feedback device 116 on the correct strut. However, it may be challenging for a user to put the measurement and feedback device 116 on the correct strut when making adjustments. Currently a user will have to look at display device 182 determine which strut to put the measurement and feedback device 116 on. However, an adjustment compliance device 104 and/or a measurement and feedback device 116 implementing adjustment compliance functionality according to some embodiments may alleviate or even completely eliminate such challenges by clearly and easily indicating to the user which strut to couple the measurement and feedback device 116 to directly on measurement and feedback device 116 (e.g., alleviating the need to look back-and-for the between the bone alignment device and computing device 110).

In various embodiments, adjustment compliance system 105 may include an adjustable medical device 160 that may be configured as an automatic adjustment device 118 configured to automatically adjust components 162a-n or assist with adjustment of components 162a-n (for example, by providing feedback or other information). In some embodiments, automatic adjustment device 118 may be or may include a component, tool, device, or other element that attaches to adjustable medical device 160 (such as to one of components 162a-n, for instance, a strut) but does not make the adjustments (for instance, provides feedback for a user or other device to make the adjustments). In other embodiments, automatic adjustment device 118 may be or may include a tool that makes the adjustments, for instance, based on feedback from measurement and feedback device 116. Non-limiting example embodiments of an automatic adjustment device 118 are described in U.S. Provisional Patent Application No. 62/906,298, entitled "Motorized Auto-Adjusting External Fixation System," which is incorporated by reference as if fully set forth in the present disclosure.

Although adjustment compliance device 104, measurement and feedback device 116, and automatic adjustment device 118 are depicted as individual devices in FIG. 1, embodiments are not so limited as adjustment compliance device 104 may be or may include measurement and feedback device 116, automatic adjustment device 118, and/or components thereof. For example, a measurement and feedback device 116 (or automatic adjustment device 118) may include indicators 112a-n and may provide compliance functions described with respect to adjustment compliance device 104 in the present disclosure. In some embodiments, automatic adjustment device 118 and/or components thereof may be coupled to, integral to, embedded in, or otherwise integrated with adjustable medical device 160.

In some embodiments, measurement and feedback device 116 may use a camera to identify the current length of the strut using markings on the strut and transmits this length back to adjustment application 148 in real time. Accordingly, a user may see the current strut length relative to the prescription, for example, displayed via display device 182. However, it may still be challenging for a user to put the measuring device on the correct strut when making adjustments. For example, the user may have to look at display 182 to determine which strut to put the measuring device on, indicated by a color and a number, which identifies a strut. For instance, each strut has an identification band with a color and a number, which the user has to match. There is no extra indication identifying the strut, leading to a risk that the user could place measurement and feedback device 116 on the wrong strut. Accordingly, adjustment compliance device 104 may operate to alleviate this risk and facilitate compliance by providing signals to a user via indicators 112a-n indicating the active strut, adjustment directionality, and/or other adjustment information.

Figure 3:
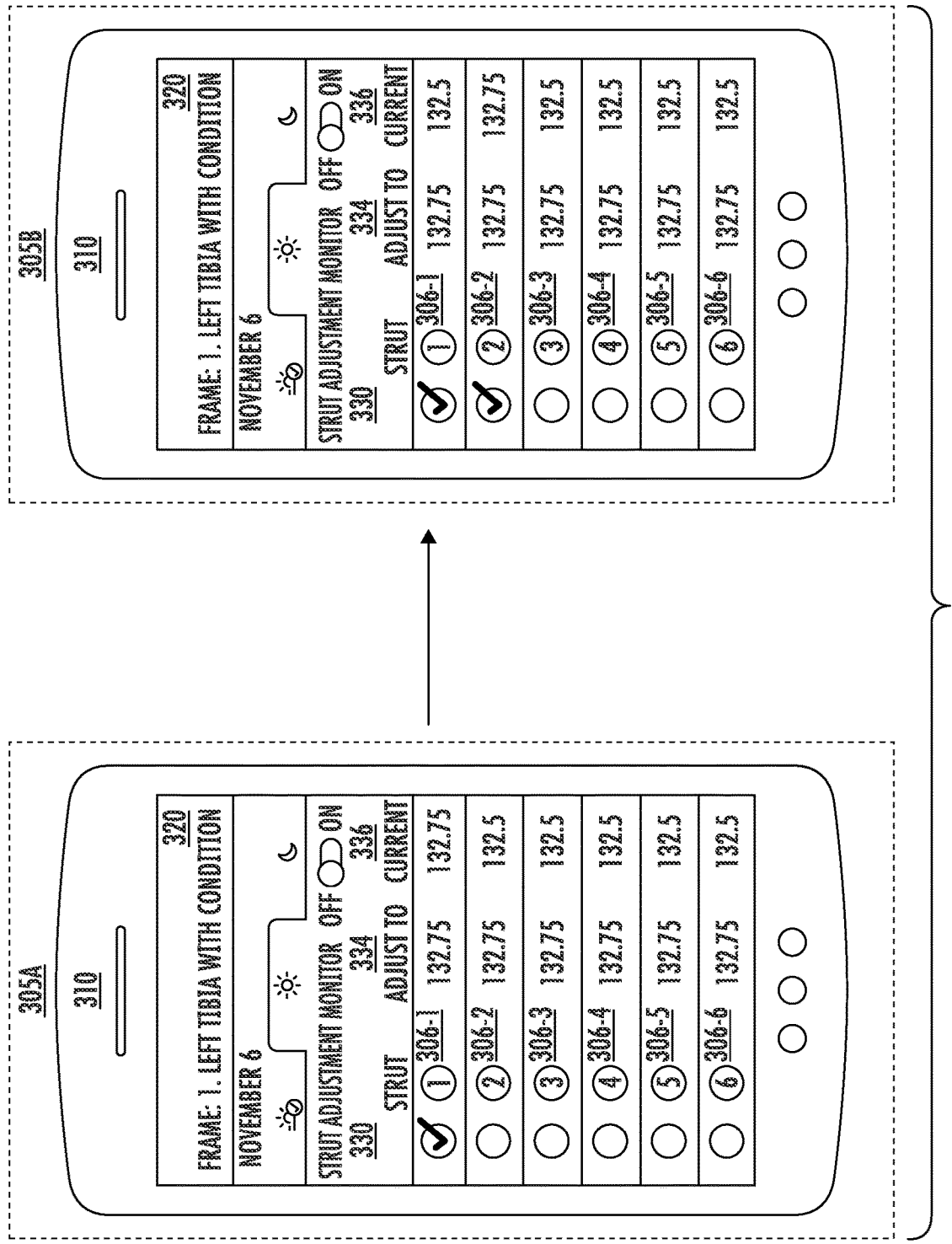
FIG. 3 illustrates a computing device depicting an embodiment of an external fixator adjustment screen.

Adjustment logic 130, for example, implemented via adjustment application 148 being executed by processor circuitry 120, may operate to perform an adjustment compliance process to facilitate proper adjustment of adjustable medical device 160 by a user according to a prescription specified in prescription information 142. Adjustment logic 130 may operate alone or in combination with adjustment indicator logic 132. A user may initiate an adjustment process, for example, via a graphical user interface (GUI) presented on display device 182. FIG. 3 illustrates a computing device depicting an embodiment of an external fixator adjustment screen. As shown in FIG. 3, a computing device 310 may present an adjustment screen 320 for a bone adjustment device having struts 1 (306-1)-6 (306-6). Adjustment screen 320 may include additional information, such as strut status 330 (i.e., active, completed, error, etc.), adjustment value (i.e., strut length after adjustment) 334, and a current value (i.e., current strut length) 336. In state 305A, strut 1 306-1 is the active strut. Adjustment logic 130 may specify indicator information 146, for example, an active component parameter, that strut 1 306-1 is the active strut. Adjustment compliance device 104 may receive indicator information 146 and activate indicator 112a to signal that strut 1 306-1 is the active strut, for example, by illuminating a red indicator light on adjustment compliance device 104 (strut 1 is associated with the color red).

Adjustment logic 130 may determine which direction strut 1 306-1 has to be turned in order to achieve the adjustment value 334 for strut 1 306-1. For example, the current value 336 (i.e., length) for strut 1 306-1 may be smaller than the adjustment value 334 (i.e., prescribed strut length for adjustment event) for strut 1 306-1, indicating that strut 1 306-1 needs to be lengthened. Adjustment logic 130 may determine indicator information 146, for example, an adjustment parameter, associated with lengthening strut 1 306-1, for instance, that strut 1 306-1 needs to be rotated in a certain direction (e.g., clockwise or counterclockwise) to achieve adjustment value 334. Adjustment compliance device 104 may receive the adjustment parameter and activate an indicator 112a-n signaling the type of adjustment for the active component (e.g., rotate clockwise).

When strut 1 306-1 has been properly adjusted, as indicated by a user selection and/or an automatic indication by measurement and feedback device 116 and/or an automatic adjustment device 118, status 330 for strut 1 306-1 may be updated to indicate that adjustment of strut 1 is complete and screen 320 may transition to state 305B for strut 2. Accordingly, adjustment logic 130 may operate to facilitate transmission of updated indicator information 146 to adjustment compliance device 104 specifying that strut 2 306-2 is the active strut and/or associated adjustment parameters.

In some embodiments, an adjustment process for a bone alignment device using adjustment compliance device 104 may include adjustment application 148, via computing device 110, wirelessly communicate to adjustment compliance device the color of the strut that adjustment compliance device 104 should be placed on. Adjustment measuring device may activate an indicator element 112a (i.e., a light element) to emit light corresponding to the indicated color to match the color of the active strut. A user may couple the adjustment compliance device 104 (and/or measurement and feedback device 116, which may be integral to the adjustment compliance device 104) to the active strut. The user may make the adjustments to the strut and remove the adjustment compliance device 104 from the strut and repeat for each additional strut.

Figure 4:
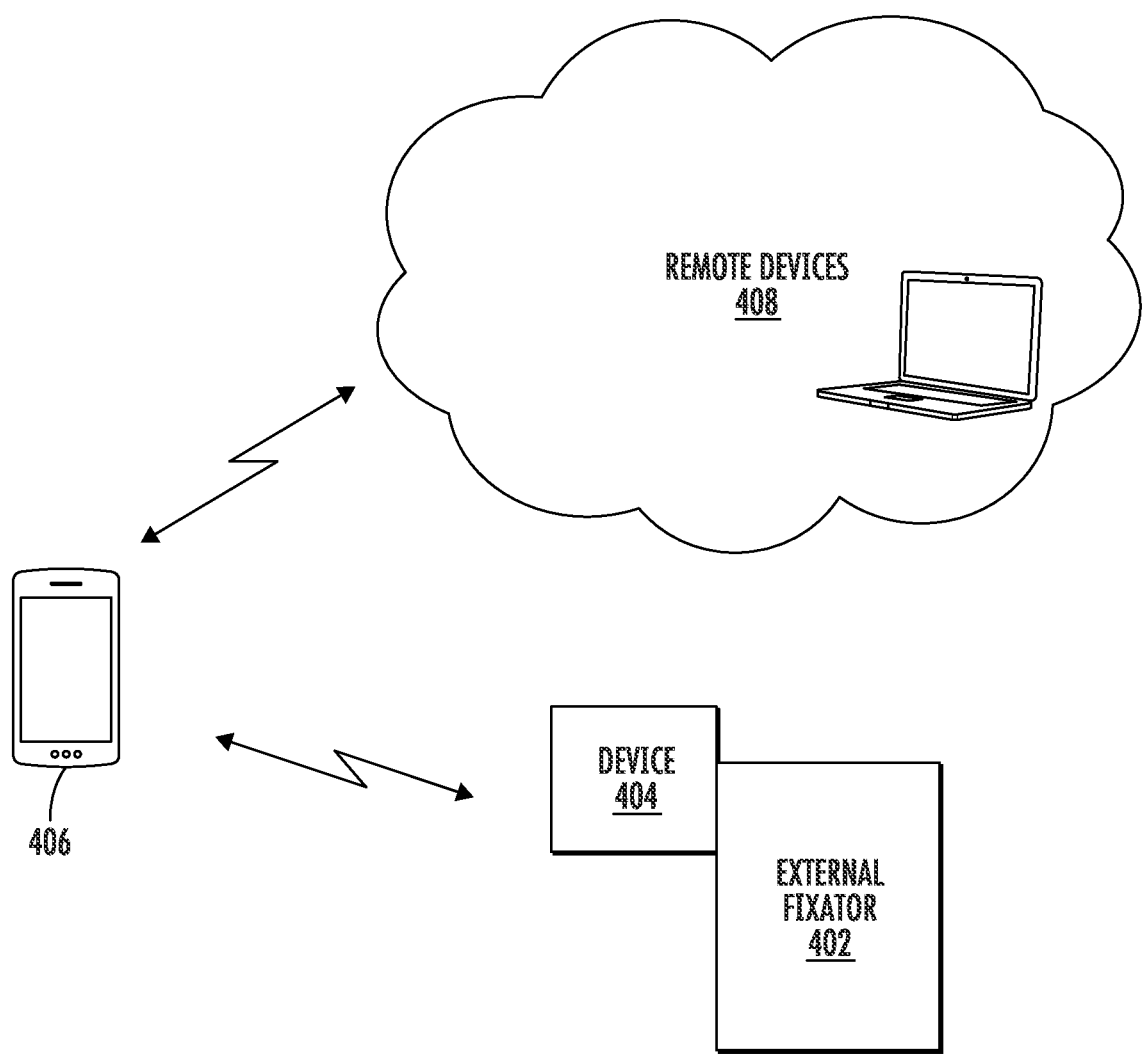
FIG. 4 illustrates an embodiment of an adjustment compliance system in accordance with one or more features of the present disclosure.

FIG. 4 illustrates an embodiment of a compliance monitoring system 400 that can be used to monitor strut compliance in connection with an external fixation system. The compliance monitoring system 400 can include an external fixator 402, an adjustment compliance device 404, and a user device 406. In various embodiments, external fixator 402 can be the bone alignment device 200 depicted in FIG. 2. Alternatively, external fixator 402 can be any other bone alignment device now known or hereafter developed.

In use, the adjustment compliance device 404 can be selectively coupled to each strut of external fixator 202 (see, for example, FIGS. 7A, 8A, 9A, 10A, 11A, 12A, and/or 13A). In one embodiment, adjustment compliance device 404 can be coupled to each strut one at a time. In use, in one embodiment, adjustment compliance device 404 can provide real-time information indicating which strut is the active strut that requires adjustment. This real-time feedback can be signaled to the user device 406 to facilitate the user adjusting the correct strut in the specified order in compliance with a predetermined prescription.

As described in greater detail in the present disclosure, in use, adjustment compliance device 404 can take on any of a number of different forms. Adjustment compliance device 404 can perform one or more of the following features, alone or together with measurement and feedback device 116 and/or an automatic adjustment device 118, among others: collect data, process data, transmit data, receive data and/or provide feedback. For example, in some embodiments, adjustment compliance device 404 can perform all of these features. Alternatively, in some embodiments, adjustment compliance device 404 can collect data and transmit data to, for example, user device 406, which can process the data and/or provide feedback. Thus arranged, in use, the adjustment compliance device 404, alone or together with measurement and feedback device 116, automatic adjustment device 118, and/or user device 406, can determine/detect what specific strut the adjustment compliance device 406, measurement and feedback device 116, and/or automatic adjustment device 118 is coupled to (e.g., strut 106-1 or 106-2, 106-3, etc.), determine if it is attached properly to the strut (e.g., indicate if the adjustment compliance device 406, measurement and feedback device 116, and/or automatic adjustment device 118 is correctly or incorrectly attached to the strut), detect the initial position of the strut (e.g., initial length of strut), detect the adjusted position of the strut (e.g., adjusted length of the strut), and/or determine change in length of the strut, transmit data to, for example, user device 406, receive data (e.g., the prescription, indicator information) from, for example, the user device 406, store a patient's prescription for adjusting the position of the various struts, compare data including the adjusted length or the adjusted position of the strut to the prescription, check for compliance with the prescription, provide feedback or indication of compliance and/or non-compliance, etc.

The adjustment compliance device 404, measurement and feedback device 116, and/or automatic adjustment device 118 can communicate directly or indirectly with user device 406, which may be any suitable user device now known or hereafter developed including, for example, an electronic device and/or a computing device such as, for example, a smartphone, a tablet, a laptop, a notebook, a netbook, a personal computer (PC), etc. In various embodiments, adjustment compliance device 404, measurement and feedback device 116, and/or automatic adjustment device 118 and user device 406 can communicate over any known wired or wireless communication standard or protocol. Example wireless connections and/or protocols may include, for example, Wi-Fi (e.g., any IEEE 802.11 a/b/g/n network), Bluetooth, Bluetooth Low Energy (BLE), Near-Field Communication (NFC), any cellular communication standard, any infrared communication protocol, USB, Lightning, etc.

The communication connectivity between adjustment compliance device 404 and user device 406 enables data or information such as, for example, measurement data, strut identification data, compliance data, indicator information, status information, and/or the like determined by adjustment compliance device 404 to be provided to the user device 406 for review by a user.

As further shown in FIG. 4, user device 406 can communicate directly or indirectly with one or more remote computing devices, remote computer networks, and/or remote cloud networks or platforms 408 (collectively referred to as "remote devices 408" without intent to be limiting). The real-time data including, for example, the measurement data, monitoring data, etc. provided by adjustment compliance device 404, measurement and feedback device 116, and/or automatic adjustment device 118 to the user device 406 and/or vice versa can be relayed to the remote devices 408. This enables a remote healthcare provider (HCP) to monitor in real-time the patient's compliance with the predetermined prescription. In an embodiment, real-time measurement and/or compliance data determined by the adjustment compliance device 404, measurement and feedback device 116, and/or automatic adjustment device 118 can be provided to one or more remote devices 408 after an adjustment to a strut of external fixator 402 has been made or after adjustments to all struts have been made. Alternatively, real-time measurement and/or compliance data determined by adjustment compliance device 404, measurement and feedback device 116, and/or automatic adjustment device 118 can be provided to one or more remote devices 408 in real-time (e.g., as adjustments to any strut are being made), thereby allowing a remote HCP to directly interact with the individual making the adjustments through communications with the user device 406.

In various embodiments, user device 406 can include software or an application (e.g., a "mobile app" or "app") that receives real-time data (e.g., measurement data, compliance data, indicator information, etc.) determined by adjustment compliance device 404, measurement and feedback device 116, and/or automatic adjustment device 118. The app on user device 406 can provide feedback to the individual adjusting the external fixator 402 as adjustments are made. The feedback can be any feedback and may include, for example, visual, tactile, and/or audible feedback. The feedback provided through the user device 406 based on real-time measurement and/or compliance data determined by the strut measurement and feedback device 404 can increase a likelihood that adjustments to the external fixator are made properly and/or comply with a prescription. In various embodiments, the user device 406, including the capabilities, features, and/or functionality of user device 406, as well as the capabilities, features, and/or functionality of any software or app provided on user device 406, can be as described in U.S. Patent Application Publication No. 2016/0092651, filed May 14, 2014, and entitled "Apparatus and Method for Administering a Medical Device Prescription," which is hereby incorporated by reference in its entirety.

The prescription, or portions thereof, for movement of the struts of the external fixator 402 can be stored remotely (e.g., on one or more remote devices 408) and/or can be stored on user device 406. The real-time measurement and/or compliance data, status information, indicator information, and/or the like determined by adjustment compliance device 404, measurement and feedback device 116, and/or automatic adjustment device 118 can be compared to the stored prescription either locally or remotely to provide feedback to the individual adjusting the struts of the external fixator 402. Accordingly, the feedback provided to the individual adjusting external fixator 402 can originate remotely (e.g., by one or more remote device 408) and can be transmitted to user device 406 or can originate locally (e.g., by the app running on user device 406).

The communication connectivity between the patient, the individual adjusting the external fixator 402, and a remote HCP by the compliance monitoring system 400 enables additional data or information to be shared. In various embodiments, visual, textual, and/or voice data or other information can be shared between user device 406 and remote computing device 408. In this way, the patient, HCP, and/or other individual adjusting external fixator 402 can communicate with a remote HCP or other individual as adjustments are being made or at any other time. In various embodiments, the patient coupled to external fixator 402 can transmit information related to pain or any other discomforts to the remote HCP. In various embodiments, the remote HCP can modify the prescription for the use of the external fixator 402 and can transmit it to the user device 406 for storage and/or use.

Figure 5:
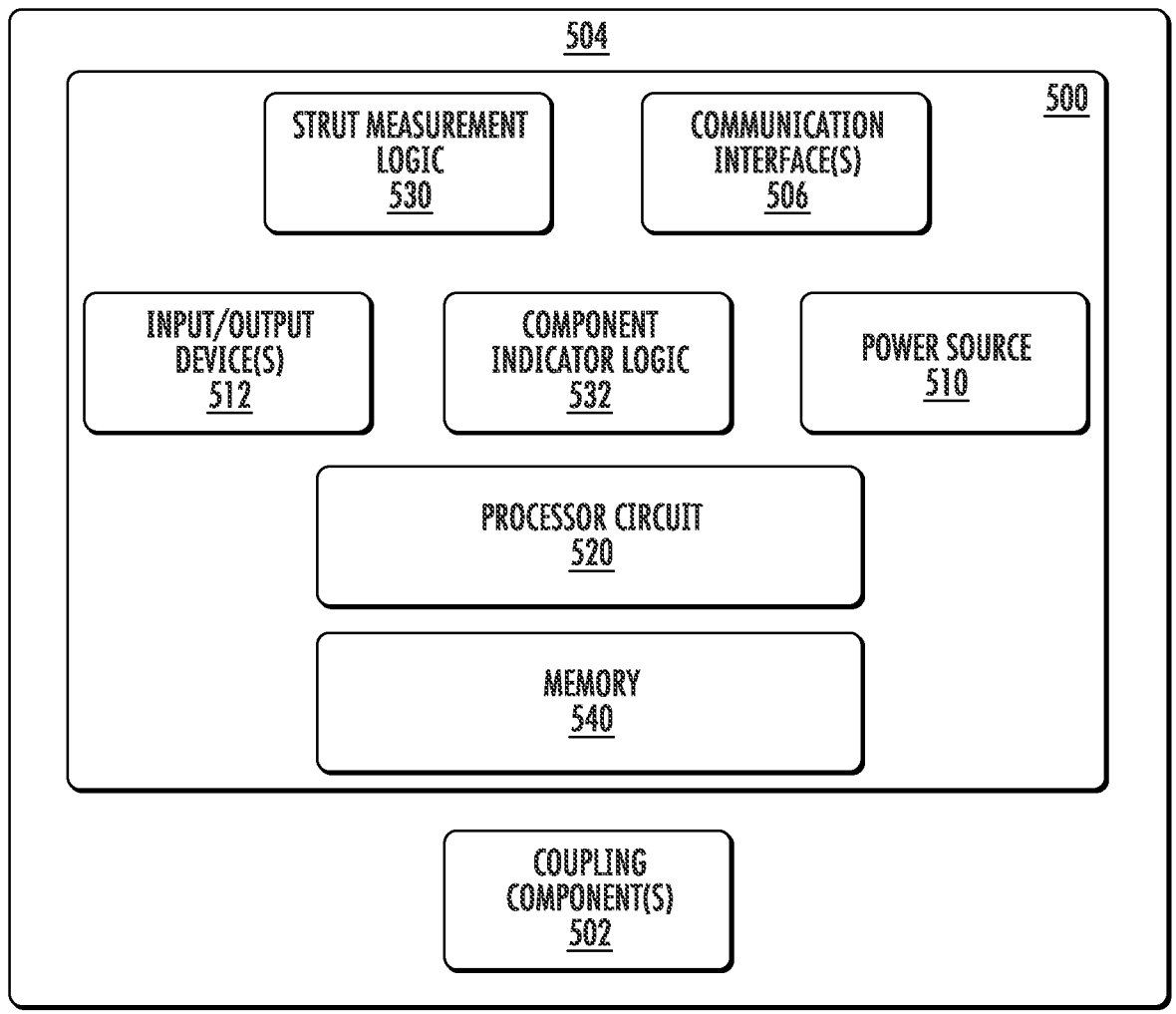
FIG. 5 illustrates a block diagram of an adjustment compliance device depicted in FIG. 4.

FIG. 5 illustrates an embodiment of an adjustment compliance device. Specifically, FIG. 5 provides a block diagram of circuitry 500 to interconnect functional components of adjustment compliance device 504. As shown, adjustment compliance device 504 may include a coupling component or module 502 for selectively coupling and detaching the adjustment compliance device 504 to and from the strut. Coupling component 502 can provide one or more physical mechanisms for coupling and decoupling adjustment compliance device 504 to a strut of an external fixator (for example, 200 or 402). Coupling component 502 can include one or more mechanical components, electrical components, electromechanical components, or any combination thereof.

Adjustment compliance device 504 may include a strut measurement component, module, or logic 530. In some embodiments, strut measurement component 530 enables adjustment compliance device 504 to determine an absolute and/or a relative positioning of a strut to which adjustment compliance device 504 is coupled. Strut measurement component 530 can also determine to which particular strut the adjustment compliance device 504 is attached. The strut measurement component can include one or more mechanical components, electrical components, electromechanical components, or any combination thereof. In some embodiments, adjustment compliance device 504 may include component indicator logic 532 operative to perform, support, or otherwise facilitate an adjustment compliance process according to various embodiments. For example, indicator logic 532 may control input/output devices 512 to operate (for instance, emit light) to indicate components to be adjusted, directionality of adjustments, and/or other adjustment information according to some embodiments.

Adjustment compliance device 504 may include a wireless communications interface 506 operative to provide interfaces for communicating with any local or remote device or network through any wireless communication technology. Wireless communications interface 506 enables adjustment compliance device 504 to wirelessly transmit and receive data or information with user device 406 and/or one or more remote computing devices 408 either directly or indirectly.

Adjustment compliance device 504 may include one or more input/output devices or components 512 operative to provide visual, audible, and/or tactile feedback to the user of the adjustment compliance device 504. In some embodiments, input/output devices 512 may be or may include indicator elements 112*a-n*. In various embodiments, input/output devices 512 can include one or more speakers, one or more light emitting diodes (LEDs), haptic devices, and/or a display (e.g., a touchscreen). In some embodiments, input/output devices 512 may include a reader device configured to read a corresponding element on a strut to determine the strut identifier. For example, input/output device 512 may include a camera (for example, to recognize a color band or number on the strut), a radio-frequency identification (RFID) scanner for reading an RFID tag positioned on the strut, a near-field communication (NFC) reader, a QR code reader, bar code reader, and/or the like. In this manner, input/output device 512 may operate to determine which strut adjustment compliance device 504 is attached to. In various embodiments, input/output devices 512 can indicate to the user of adjustment compliance device 504 whether or not adjustment compliance device 504 is being used properly (e.g., if adjustment compliance device 504 is attached properly or improperly) and/or can indicate whether a strut measurement is in progress, is complete, and/or was done incorrectly or erroneously.

Adjustment compliance device 504 may include a power source 510 that may be or may include electrical power connections and/or a battery. Power source 510 may provide power to any of the constituent functional components of the adjustment compliance device 504 depicted in FIG. 5. In various embodiments power source 510 can be a rechargeable battery or, alternatively, a replaceable battery. In some embodiments, power source 510 may be or may include an external power source, such as a mobile computing device (for instance, via USB or Thunderbolt), an external battery, a power outlet, and/or the like.

Adjustment compliance device 504 may further include a processor circuit 520 and an associated memory component 530. Memory component 530 may store one or more programs for execution by processor circuit 520 to implement one or more functions or features of adjustment compliance device 504 as described herein. Processor circuit 520 may be implemented using any processor or logic device. Memory component 530 can be implemented using any machine-readable or computer-readable media capable of storing data, including both volatile and non-volatile memory.

Processor circuit 520 may implement the functionalities of any of the components depicted in FIG. 5 or may control or adjust operation of any of the depicted components. Each component depicted in FIG. 5 may be coupled to processor circuit 520 as well as any other depicted component. For instance, processor circuit 520 may, in some embodiments, determine indicator information, for example, transmitted via user device 506, and store the indicator information in memory 540. In some embodiments, the indicator information may include an active strut and/or a direction of rotation for adjusting the active strut. In various embodiments, process circuit 520 may determine whether adjustment compliance device 504 is communicating with user device 506 and may activate/deactivate a connection indicator input/output device 512 accordingly. The depicted components may be implemented in hardware or software as appropriate, or any combination thereof.

FIG. 6 illustrates a block diagram of an embodiment of an adjustment compliance device. As shown in FIG. 6, adjustment compliance device 604 may include a main body or housing 610 associated with one or more input/output elements 612*a-g*. In some embodiments, certain of input/output elements 612*a-g* may be or may include indicator elements configured to present indicator information to a user. For example, indicator element 612*a* may indicate a power state of adjustment compliance device 604, such as whether adjustment compliance device 604 is powered-on, a charge state, and/or the like. Indicator element 612*b* may operate as a communication status indicator to indicate whether adjustment compliance device 604 is properly communicating via a certain protocol (e.g., Bluetooth, WiFi, and/or the like) and/or with a device (e.g., user device 406).

Indicator element 612*c* may be a component indicator operative to indicate an active component of an adjustment process. In various embodiments, indicator element 612*c* may provide a signal specifying the active component. For example, indicator element 612*c* may be a light element configured to emit light having a color corresponding with an active strut of a bone adjustment device (for instance, a red light for strut 1). In another example, indicator element 612*c* may include a set of light elements, with one light for each component, configured to emit light from the light element corresponding to the active component (for example, light 3 for strut 3). In some embodiments, the set of light elements may include a row or ring of colored lights (for instance, one light for each strut). For example, a mechanism with a light source and a series of colored mediums that rotate in front of the light source to change the color of the light projected from the device may be used to indicate the active component.

In another example, indicator element 612*c* may include a screen device (LCD and/or the like) configured to display information indicating the active component (e.g., strut number, strut location, strut color, and/or the like) and/or other information including, without limitation, current strut length, desired strut length, adjustment direction, over/under adjustment, strut identification, battery status, wireless connection status, wired connection status, strut adjustment reminders, strut change out notifications, errors, diagnostic information, total adjustments, and/or the like.

In a further example, indicator element 612*c* may include a speaker device configured to provide an audible signal, such as projecting the name of the active component, a series of tones associated with the active component, and/or other information including, without limitation, strut to be attached to, step-by-step directions for applying and using the measurement device, current strut length, desired strut length, adjustment direction, over/under adjustment, strut identification, battery status, wireless connection status, wired connection status, strut adjustment reminders, strut change out notifications, errors, diagnostic information, total adjustments, and/or the like. Embodiments are not limited in this context.

Indicator element 612*d* may operate as an adjustment direction indicator, for example, to specify the direction of rotation of a strut or whether the strut requires lengthening or shortening. For example, indicator element 612*d* may include a rotating graphic, a circular light, a rotating light, and/or the like configured to emit light in a manner indicating a direction of rotation. In another example, indicator element 612d may be activated to indicate that the active strut should be adjusted to lengthen or shorten the strut. For instance, if strut 1 of a bone applicator requires rotation in a clockwise manner, indicator element 612c may be activated to indicate strut 1 is the active component and indicator element 612d may be activated to indicate clockwise rotation.

Indicator element 612e may operate to indicate an error state of adjustment compliance device 604. For example, adjustment compliance device 604 may receive erroneous or undecipherable adjustment information such that adjustment compliance device 604 cannot determine an adjustment parameter, such as the active strut, direction of rotation, and/or the like. In some embodiments, adjustment compliance device 604 may determine which component it is coupled to and which component is the active component (or may receive this information from user device 406). If adjustment compliance device 604 determines that it is coupled to the wrong component during an adjustment (i.e., a strut that is not the active strut), adjustment compliance device 604 may activate an error condition. Indicator element 612e may be activated to signal an error condition (and, in some embodiments, the type of error condition) to the user. In various embodiments, a companion error message may be displayed on user device 406.

In some embodiments, one or more of indicator elements 612a-g may include haptic or tactile indicator elements configured to indicate indicator information including, without limitation, the active component, adjustment direction, current measurement reading, strut to be attached to, step-by-step directions for applying and using the measurement device, and/or the like.

In various embodiments, one or more input/output devices may be separate from the main body 610 of adjustment compliance device 604. In various embodiments, a secondary housing or body 630 may contain one or more input devices 612f and/or components of adjustment compliance device 604 (for instance, hardware and/or software elements). In some embodiments, an input/output element 612g (e.g., a camera) may be an individual element arranged external to main housing 610. In some embodiments, external components, such as 630 and 612g may be connected to main housing 610 via connector elements 622. In some embodiments, connector elements 622 may include communication elements, such as wires and/or the like that may be used to transfer communication signals, data, power, and/or the like between external components and main housing 610.

Adjustment compliance device 604 may include one or more coupling components 602a-n to attach, affix, mount, engage, or otherwise couple main housing 610 to an adjustable medical device and/or components thereof, such as a strut of a bone adjustment device. Coupling components 602a-n may include clips, c-clips, clamps, hangers, shackles, loops, hooks, snap-fit elements, friction-fit elements, and/or the like. In various embodiments, components external to main body 610 (such as elements 630 and 612g) may include their own individual coupling components 602p, 602q.

Various embodiments of adjustment compliance devices are described herein. The various embodiments may vary by shape, size, functionality, form factor, and/or other characteristics. In addition, the various embodiments may vary by implementation of the constituent components, for example, described in relation to FIGS. 1, 2, and 4-6. Features and/or functionalities of any described embodiment can be combined or used in combination with features and/or functionalities of any other embodiment described herein as will be appreciated by one skilled in the relevant arts.

Figure 7B:
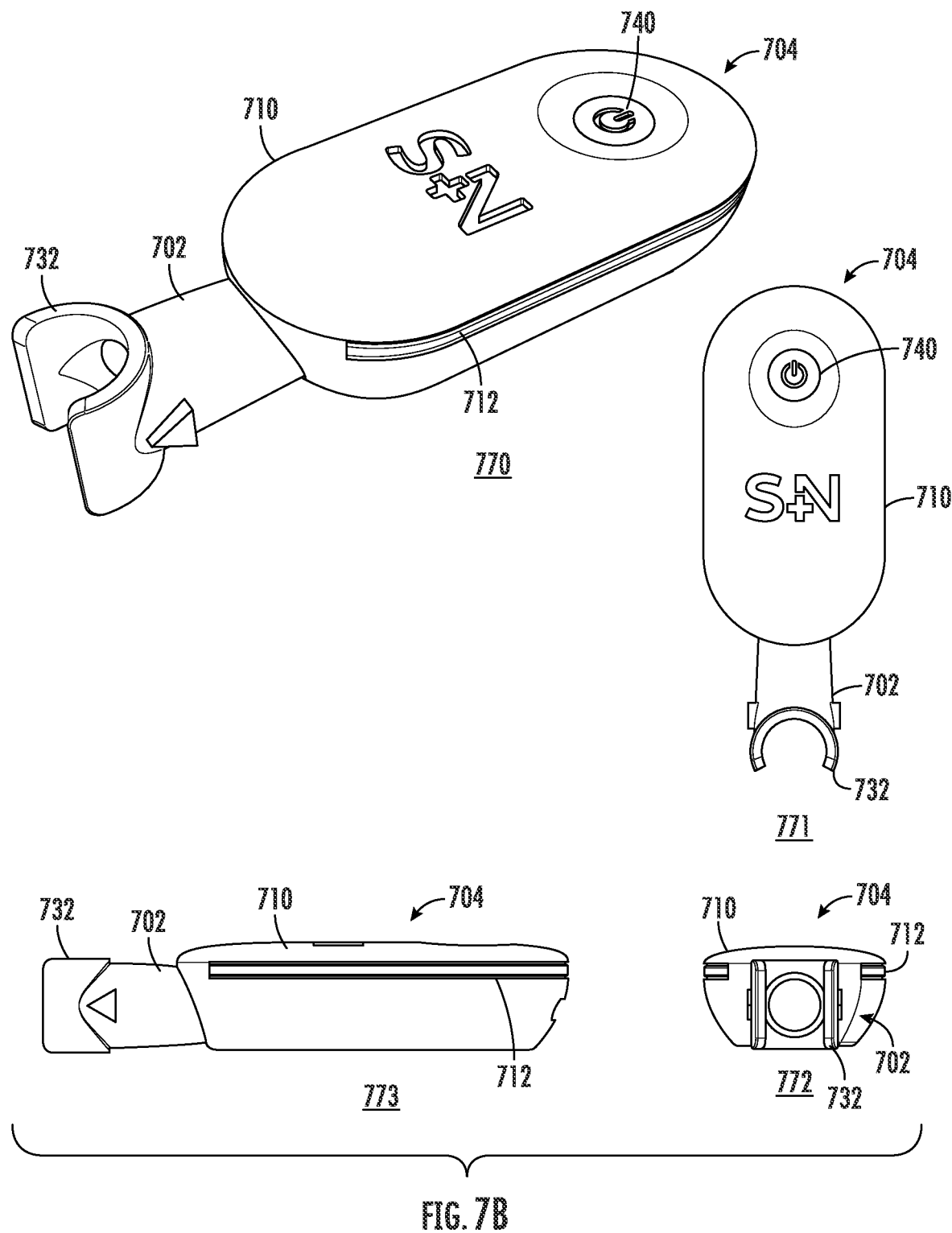

FIGS. 7A and 7B illustrate a first embodiment of an adjustment compliance device. As shown in FIG. 7A, a medical adjustment device may include a bone alignment device 760 coupled to a portion of a patient 752, such as portions of the bones of the lower leg. In some embodiments, bone alignment device 760 may include a bone alignment device the same or similar as bone alignment device 200 of FIG. 2. In some embodiments, bone alignment device 760 may be a Taylor Spatial Frame™ device. In various embodiments, bone alignment device 760 may include a plurality of struts 762a-c. Although three struts are depicted in FIG. 7A, bone alignment device 760 may include more or less struts according to some embodiments.

Adjustment compliance device 704 may include a main body 710 housing a power button 740 to implement powering on/off adjustment compliance device 704. An indicator element (or light) 712 may include a light element configured to emit light of different colors to correspond to an active strut 762a-c. For example, strut 762a (for instance, strut 5) is associated with a blue color band. Adjustment compliance device 704 may cause indicator element 712 to emit blue light to signal that strut 762a is active. In various embodiments, adjustment compliance device 704 may include a coupling component 702, for example, in the form of a clip configured to couple adjustment compliance device 704 to a portion of a strut 762a-c. In some embodiments, at least a portion of the hardware and/or software required to operate adjustment compliance device 704 (see, for example, FIG. 4) may be arranged within main body 710.

FIG. 7B depicts various views of adjustment compliance device 704, such as a top perspective view 770, a top view 771, a back (or coupling side) view 772, and a side view 773.

Figure 8B:
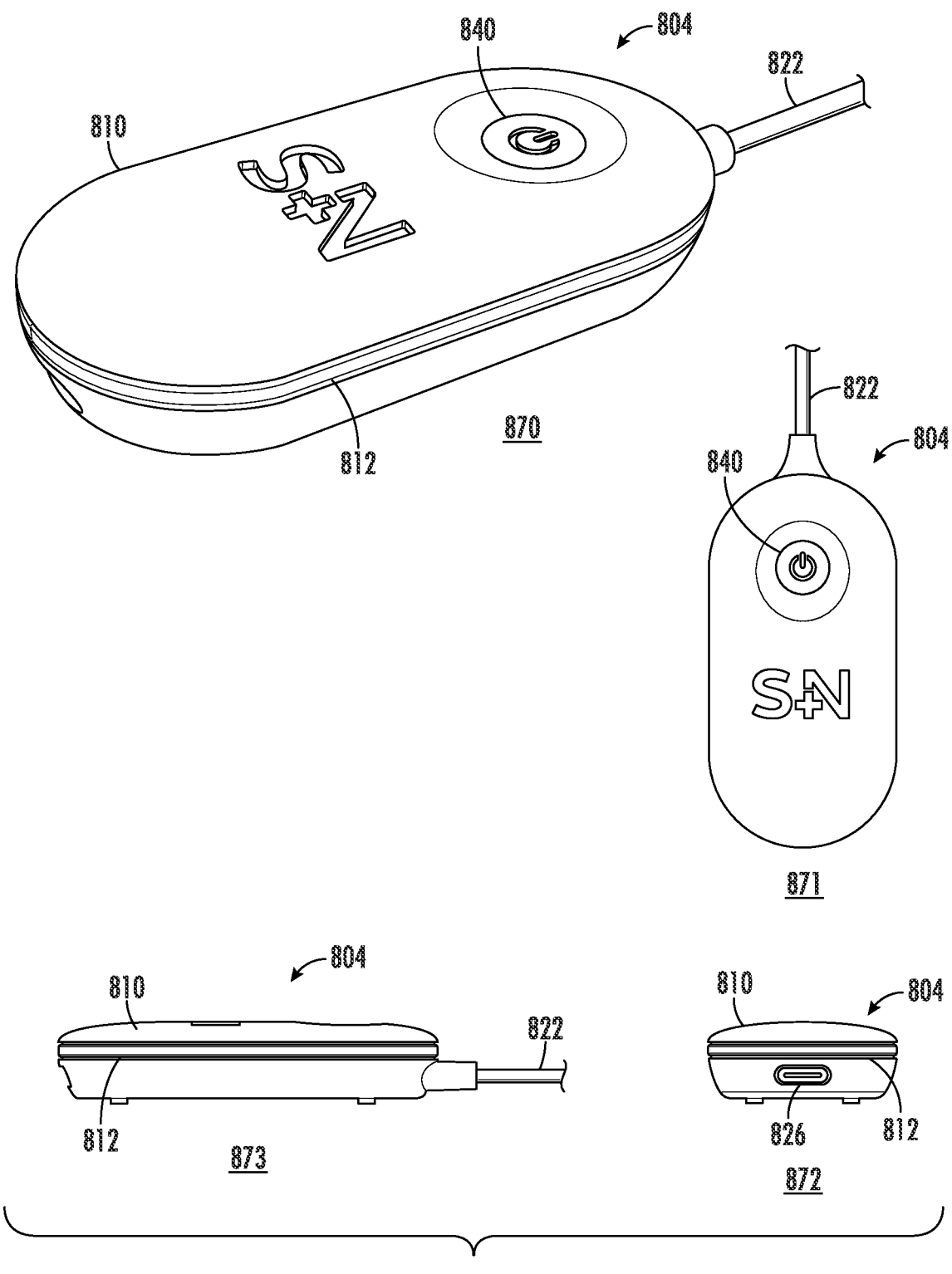

FIGS. 8A and 8B illustrate a second embodiment of an adjustment compliance device. As shown in FIG. 8A, an adjustment compliance device 804 may include a main body 810, a power button 840, and an indicator element 812 configured to emit light in a color corresponding to an active strut 762a-c. Adjustment compliance device 804 may include a secondary housing 830 coupled to strut 762a via coupling component 802. In some embodiments, secondary housing 830 may include at least a portion of the hardware and/or software required to operate adjustment compliance device 804. For example, secondary housing 830 may include a camera or other device for operating adjustment compliance device 804. Main body 810 and secondary housing 830 may be coupled via communication element 822, for instance, forming a wired connection.

FIG. 8B depicts various views of adjustment compliance device 804, such as a top perspective view 870, a top view 871, a front view 872, and a side view 873. Referring to front view 872, in some embodiments, adjustment compliance device 804 may include a port 826, for example, for charging and/or communicating with adjustment compliance device 804. For example, port 826 may include a Lightning port or a mini or micro USB port for charging adjustment compliance device 804 and/or connecting adjustment compliance device 804 to a user device 406.

Figure 9B:
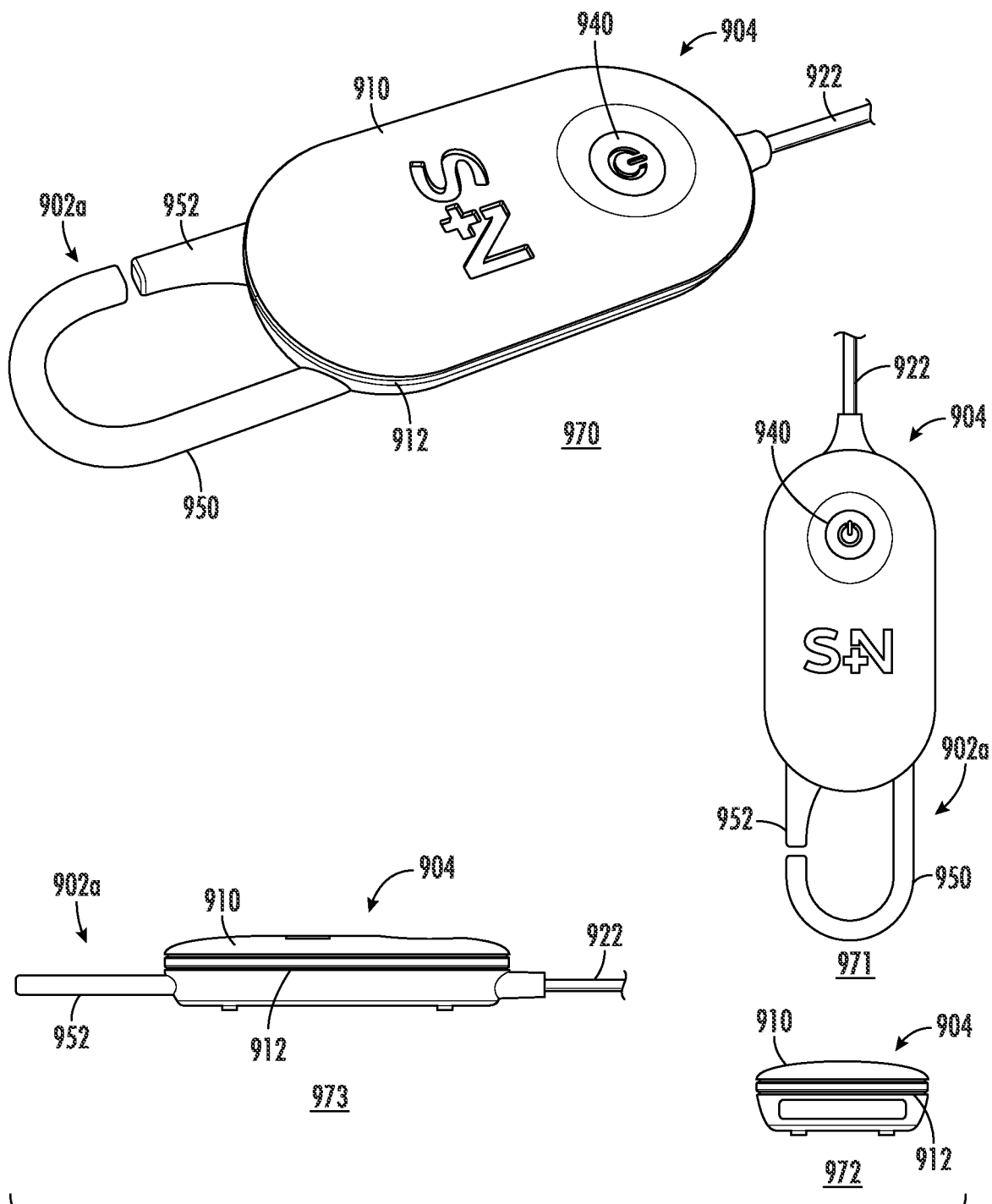

FIGS. 9A and 9B illustrate a third embodiment of an adjustment compliance device. As shown in FIG. 9A, an adjustment compliance device 904 may include a main body 910, a power button 940, and an indicator element 912 configured to emit light in a color corresponding to an active strut 762a-c. Adjustment compliance device 904 may include a secondary housing 930 coupled to strut 762*a* via coupling component 902*b*. Main body 910 may include coupling component 902*a*, for example, in the form of a hook or hook-like element configured to allow main body 910 to hang from a frame portion 936 of bone alignment device 760. Main body 910 and secondary housing 930 may be coupled via communication element 922, for instance, forming a wired connection FIG. 9B depicts various views of adjustment compliance device 904, such as a top perspective view 970, a top view 971, a front view 972, and a side view 973. As shown in FIG. 9B, coupling component 902*a* may be formed of a hook portion 950 (for example, formed of a strong, non-flexible material, such as metal) and an elastomeric door portion 952.

Figure 10A:
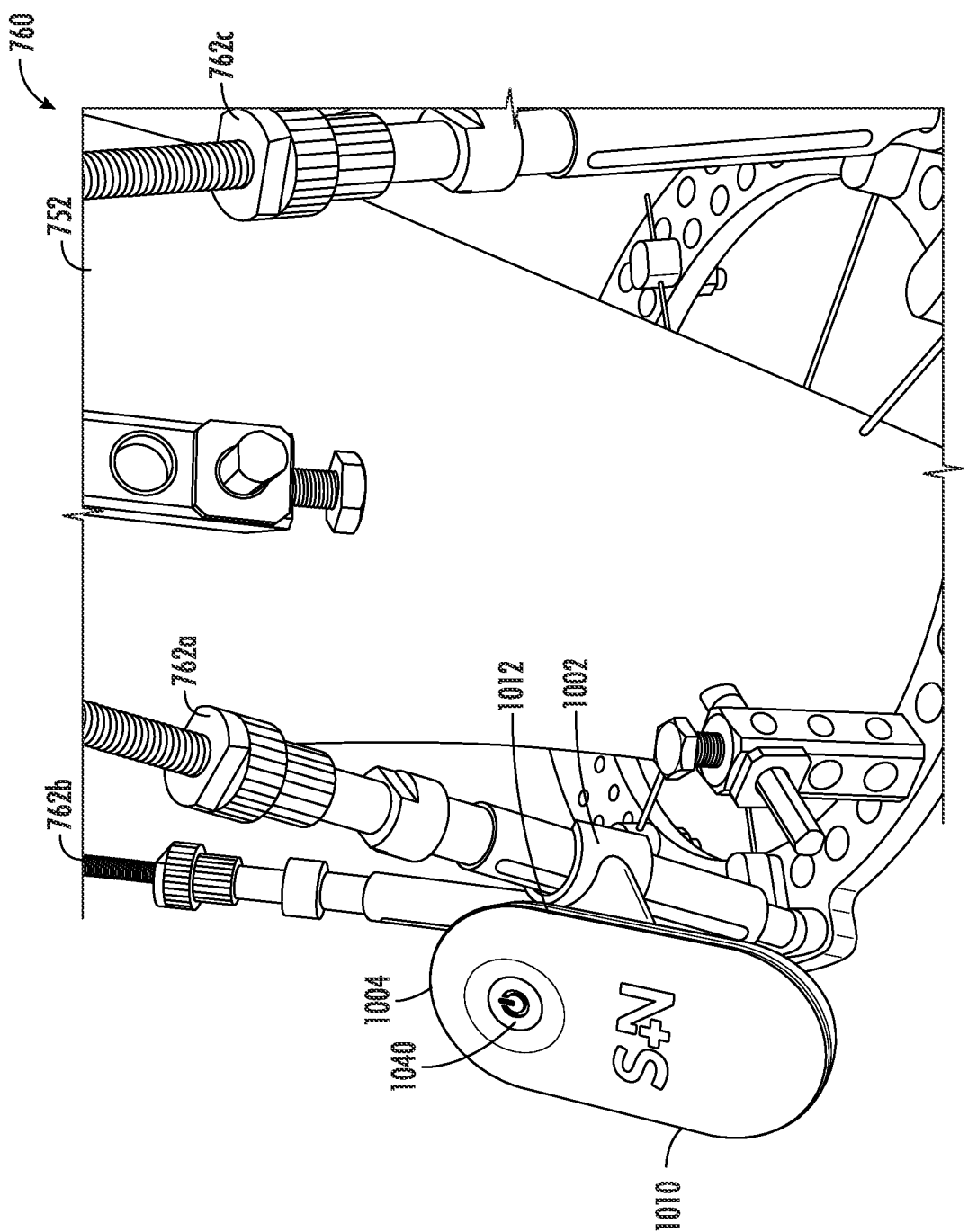
FIGS. 10A and 10B illustrate a fourth embodiment of an adjustment compliance device.
Figure 10B:
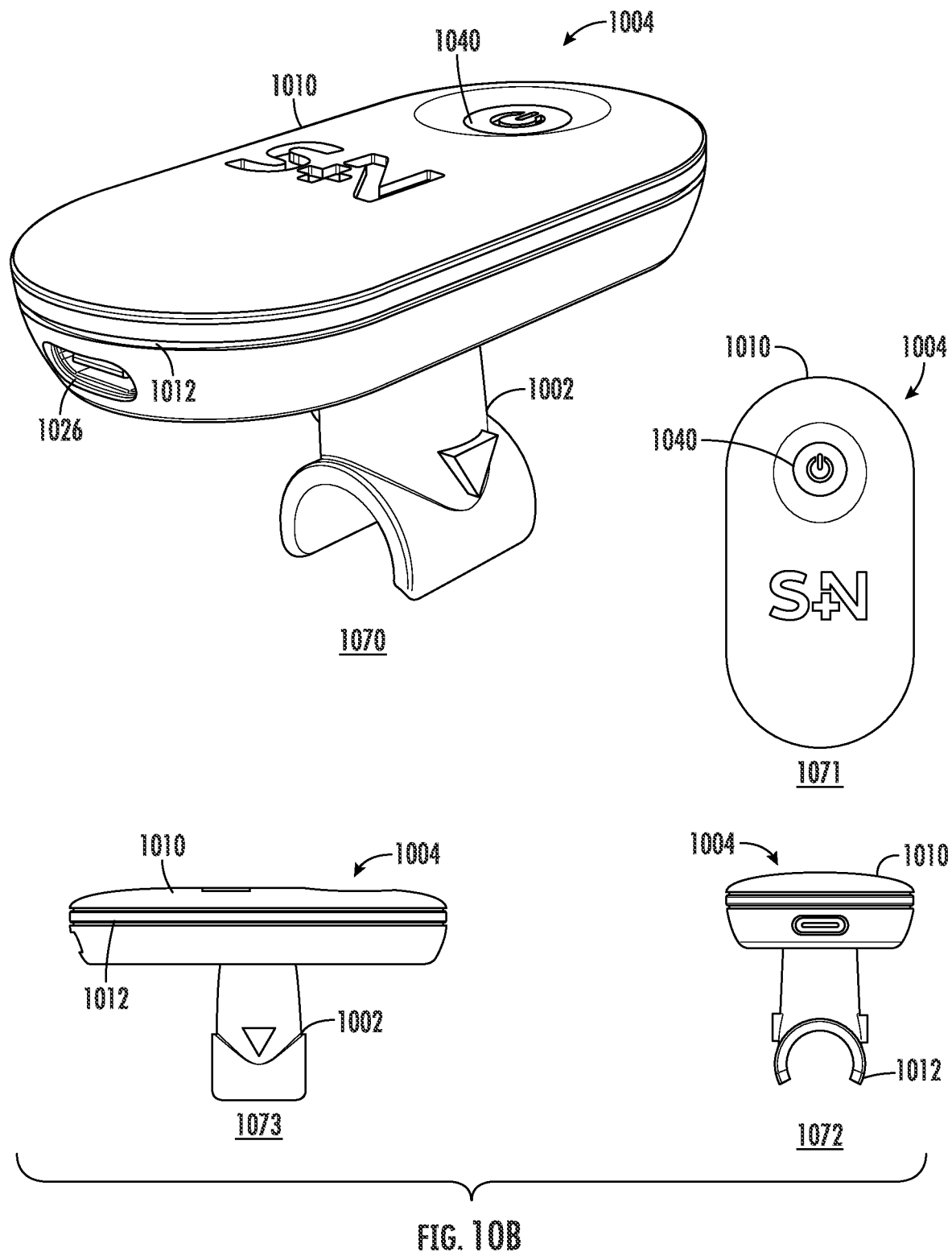

FIGS. 10A and 10B illustrate a fourth embodiment of an adjustment compliance device. As shown in FIG. 10A, an adjustment compliance device 1004 may include a main body 1010, a power button 1040, and an indicator element 1012 configured to emit light in a color corresponding to an active strut 762*a-c*. Main body 1010 may be coupled to strut 762*a* via coupling component 1002, for example, in the form of a snap-fit clip arranged on a back side of main body 1010.

FIG. 10B depicts various views of adjustment compliance device 1004, such as a top perspective view 1070, a top view 1071, a front view 1072, and a side view 1073.

Figure 11A:
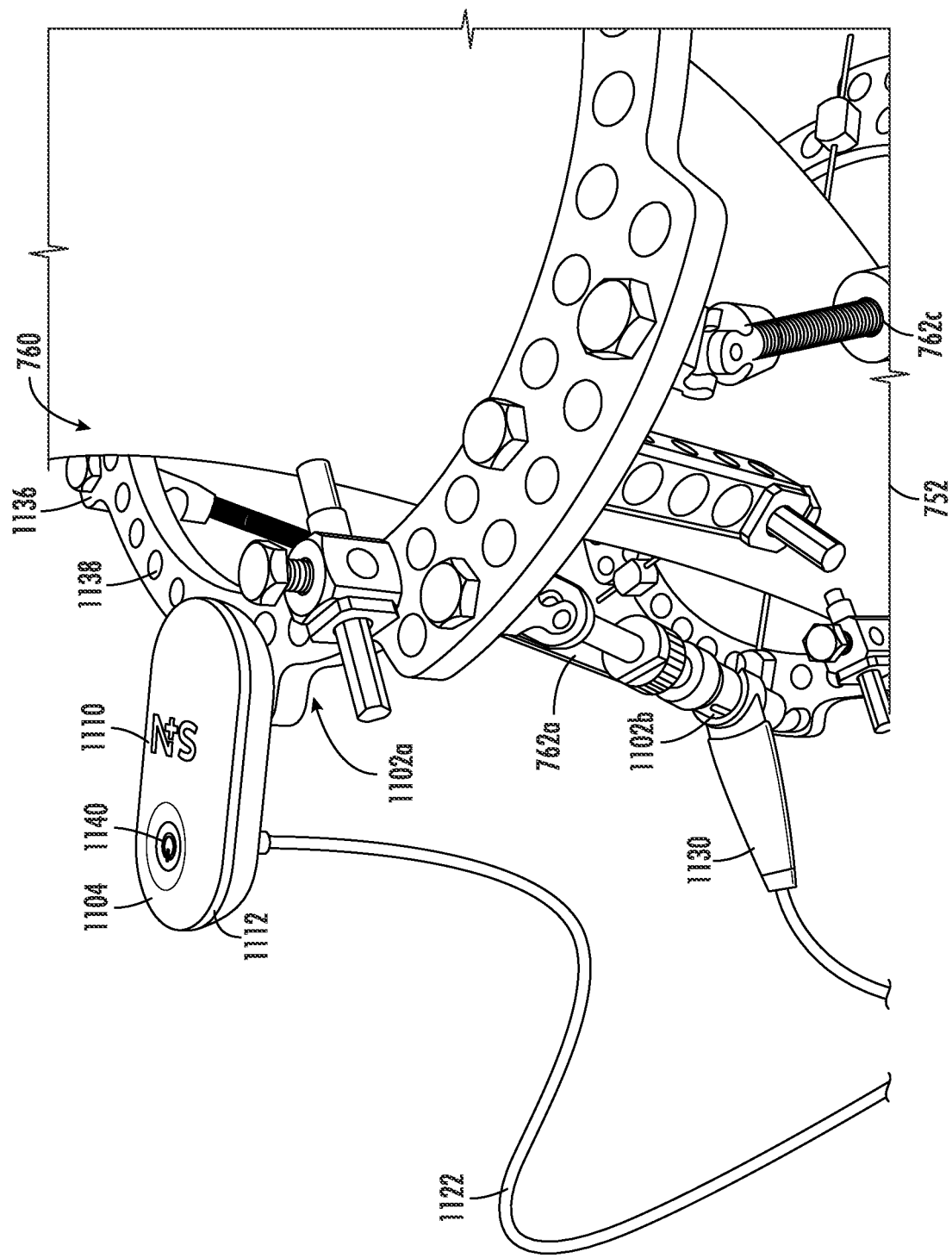
FIGS. 11A and 11B illustrate a fifth embodiment of an adjustment compliance device.
Figure 11B:
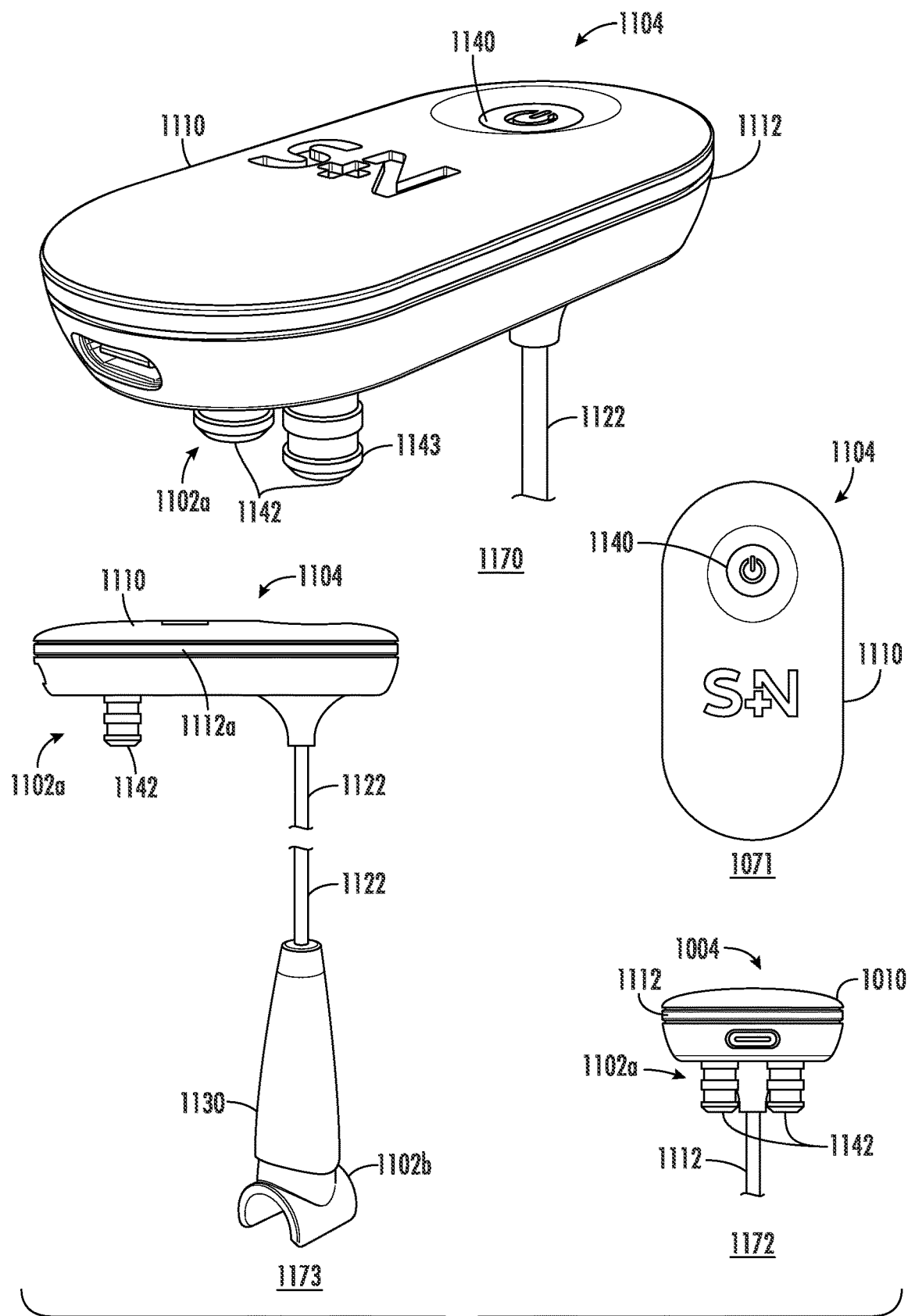

FIGS. 11A and 11B illustrate a fifth embodiment of an adjustment compliance device. As shown in FIG. 11A, an adjustment compliance device 1104 may include a main body 1110, a power button 1140, and an indicator element 1112 configured to emit light in a color corresponding to an active strut 762*a-c*. Adjustment compliance device 1104 may include a secondary housing 1130 coupled to strut 762*a* via coupling component 1102*b*, such as a snap-fit clip. Main body 1110 may include coupling component 1102*a* configured to releasably engage openings 1138 of a frame 1136 of bone alignment device 760. Main body 1110 and secondary housing 1130 may be coupled via communication element 1122, for instance, forming a wired connection. In some embodiments, secondary housing 1130 may include at least a portion of the hardware and/or software required to operate adjustment compliance device 1104.

FIG. 11B depicts various views of adjustment compliance device 1104, such as a top perspective view 1170, a top view 1171, a front view 1172, and a side view 1173. As shown in FIG. 11B, coupling component 1102*a* may be formed of one or more posts 1142 configured to engage openings 1138 of frame 1136 of bone alignment device 760. For example, a first portion 1143 of post 1142 may be forced into opening 1138 to seat post 1142 within opening 1138. Post 1142 and/or portions thereof may be formed of a flexible material configured to facilitate gripping an inner portion of opening 1138 by post 1142.

Figure 12B:
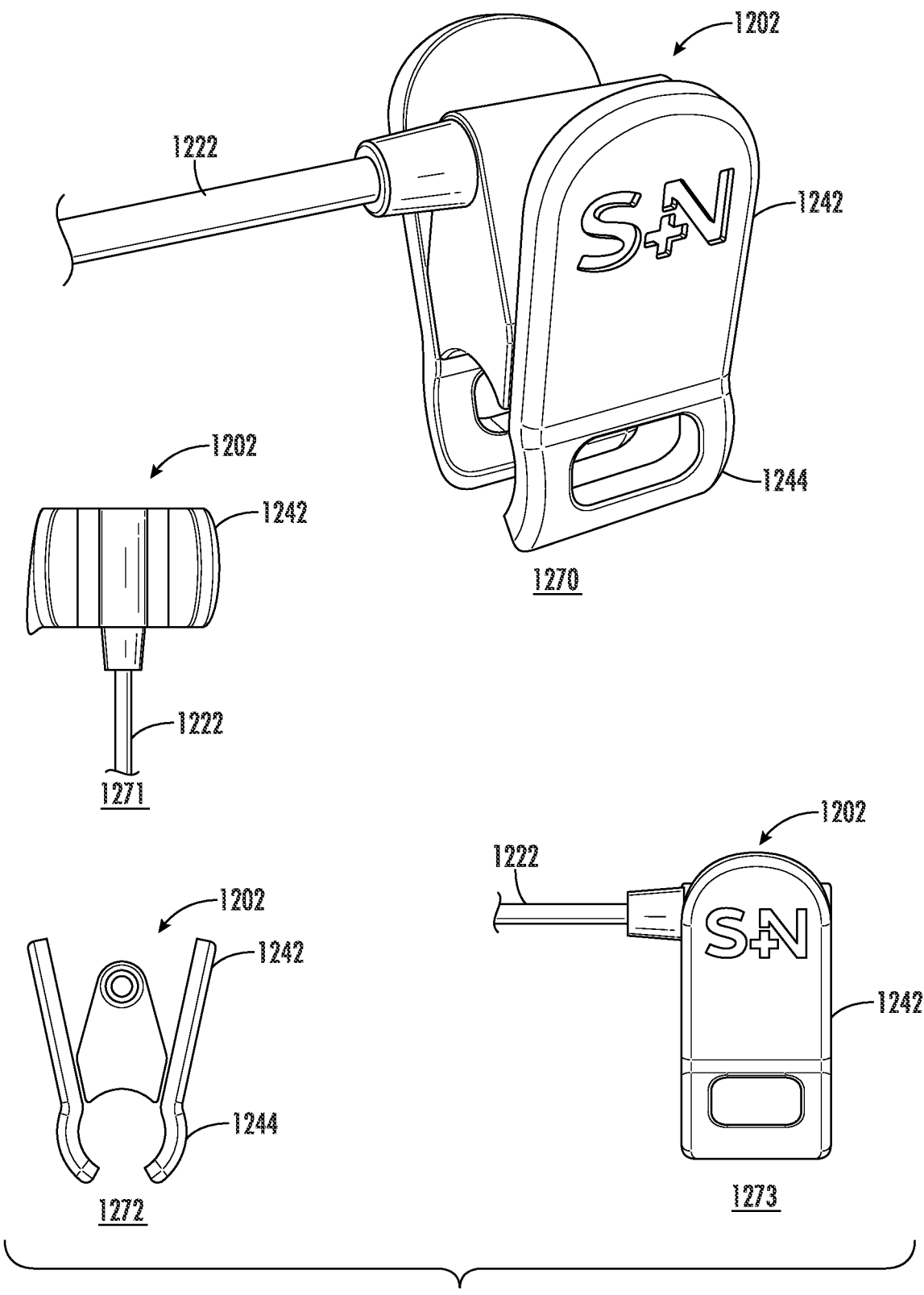

FIGS. 12A and 12B illustrate a sixth embodiment of an adjustment compliance device. As shown in FIG. 12A, an adjustment compliance device 1204 may include a clip coupling component 1202 to a portion of adjustment compliance device 1204 to strut 762*a* (i.e., the active strut). Adjustment compliance device 1204 may include a user device 1206, such as a smart phone or other mobile computing device, operative to perform the functions of adjustment compliance device 1104, such as indicating the active strut, adjustment parameters, and/or the like. In some embodiments, at least a portion of the functionality of adjustment compliance device 1204 may be performed via hardware and/or software arranged in coupling component 1202. For example, coupling component 1202 may include a camera device, a light element, and/or the like. In various embodiments, coupling component 1202 and user device 1206 may be coupled via communication element 1222, for instance, forming a wired connection.

FIG. 12B depicts various views of coupling component 1202, such as a top perspective view 1270, a top view 1271, a front view 1272, and a side view 1273. As shown in FIG. 12B, coupling component 1202 may include a pair of prongs 1242 that may be squeezed to expand clip portion 1244 to fit around a portion of strut 762*a-c*; release of prongs 1242 may allow clip portion 1244 to retract around strut 762*a-c* to rigidly attach coupling component 1202 to strut 762*a-c*.

Figure 13A:
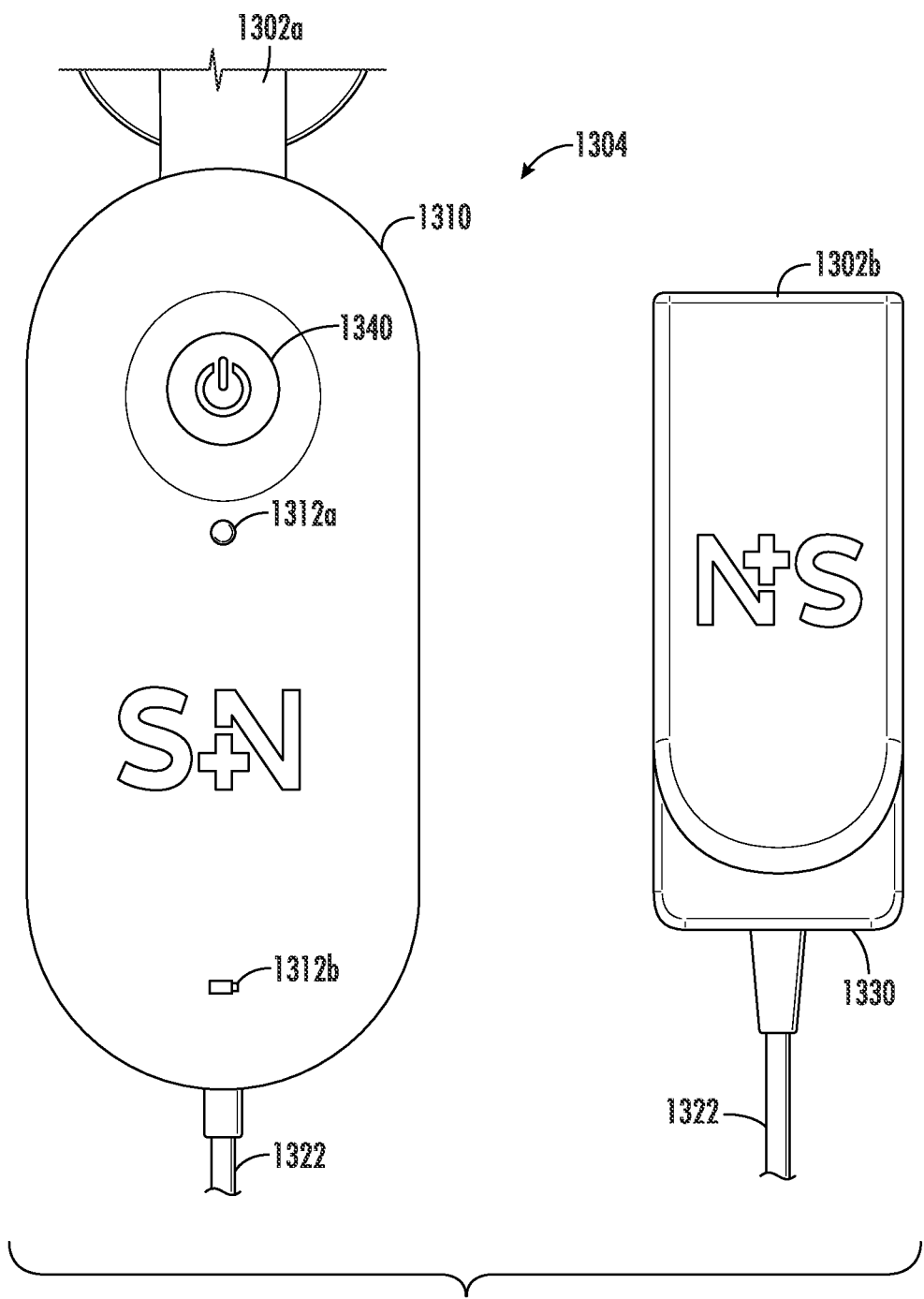
FIGS. 13A-13C illustrate a seventh embodiment of an adjustment compliance device.
Figure 13B:
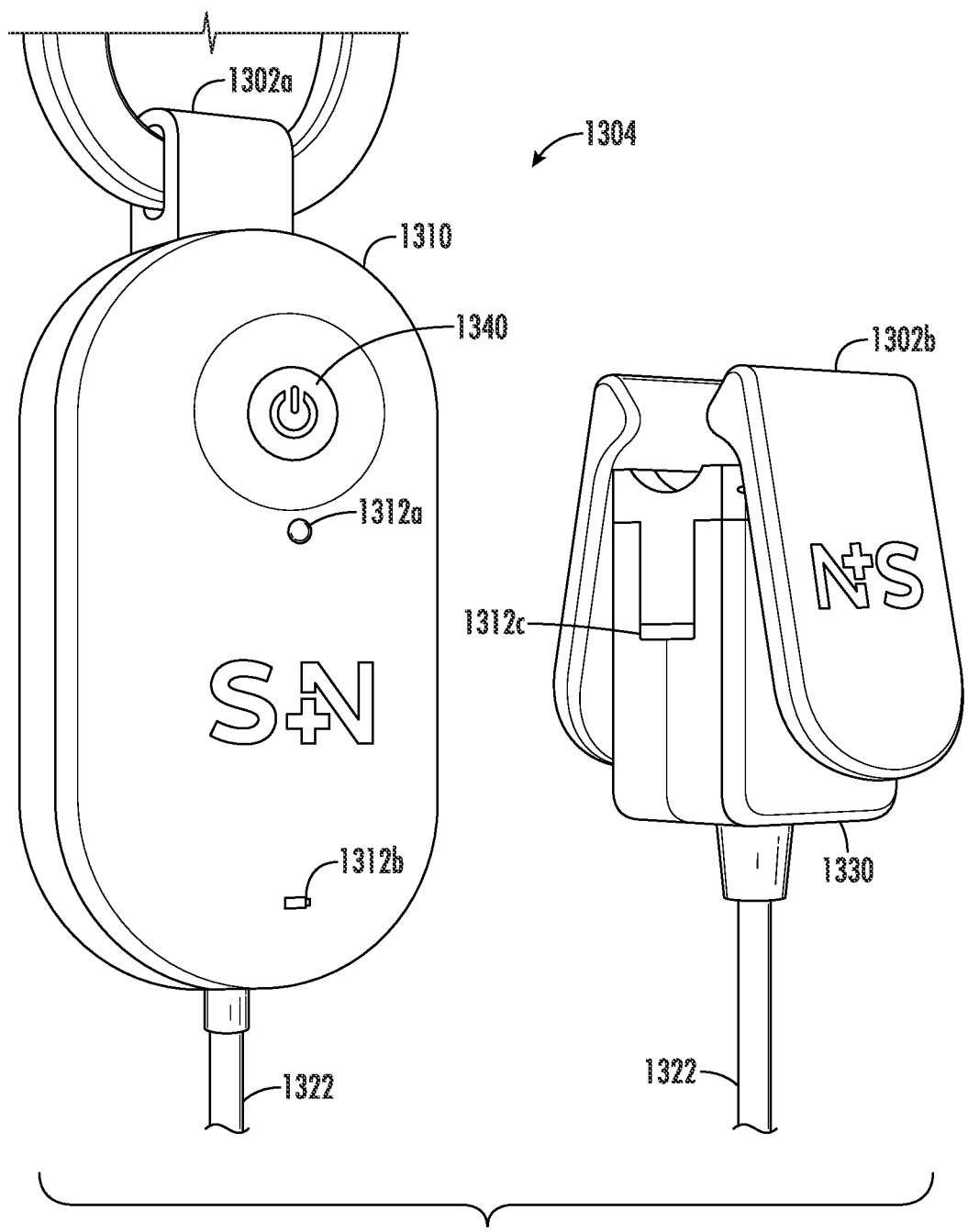
Figure 13C:
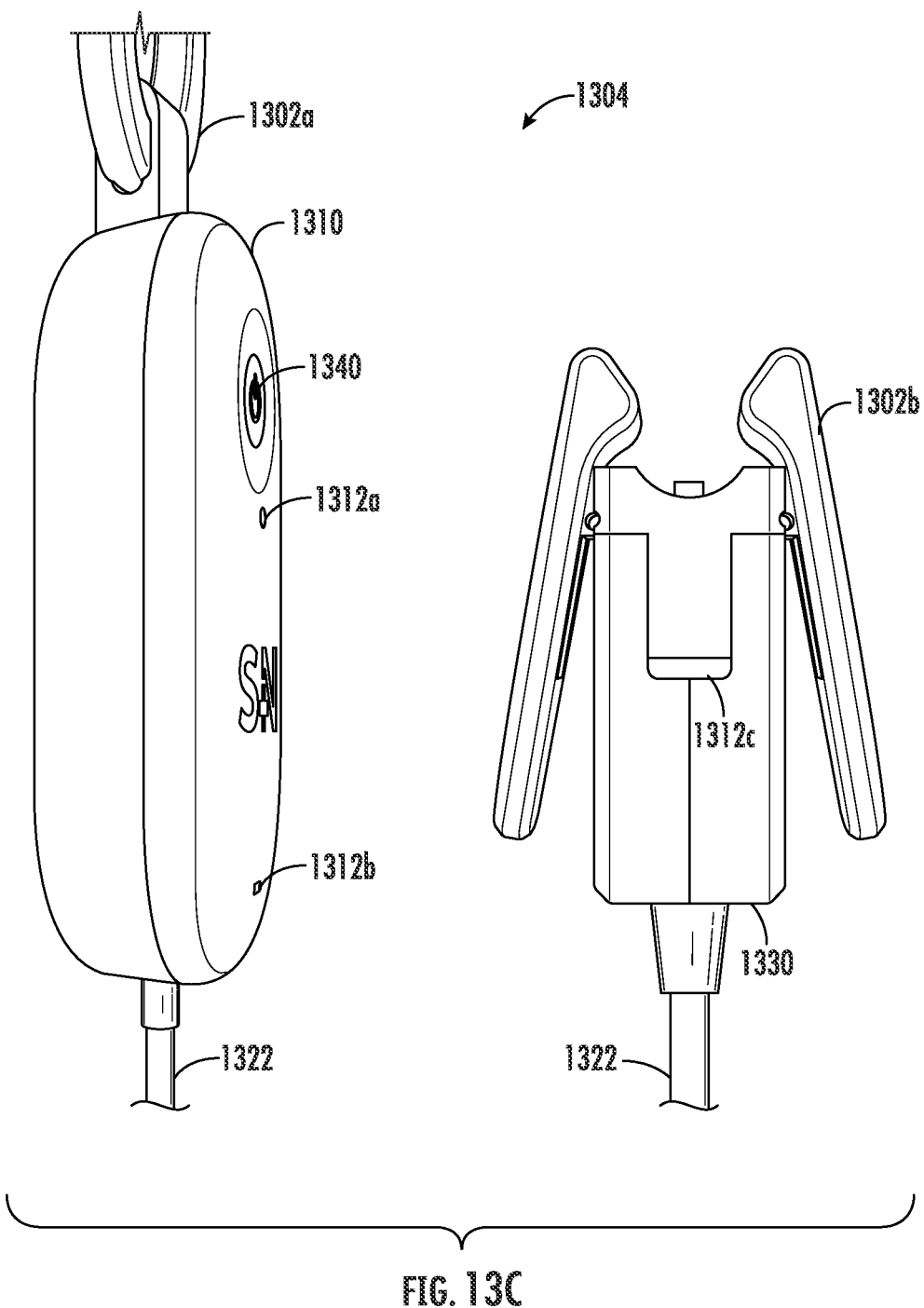

FIGS. 13A-13C illustrate a seventh embodiment of an adjustment compliance device. As shown in FIGS. 13A-13C, an adjustment compliance device 1104 may include a main body 1310 housing a power button 1340 and indicator elements 1312*a*, 1312*b*. Indicator element 1312*a* may operate to indicate an active component, such as the next strut to be adjusted for a bone alignment device. For example, indicator element 1312*a* may be a light element configured to emit light of a color corresponding to the active strut. Indicator element 1312*b* may be a power status indicator, for example, to indicate a level of charge of adjustment compliance device 1304.

In some embodiments, adjustment compliance device 1304 may include a coupling component 1302*a*, for example, in the form of a hook operative to hang or otherwise support main body 1310 on a frame of a bone alignment device. Adjustment compliance device 1304 may include a secondary housing 1330 having indicator element 1312*c*. For example, indicator element 1312*c* may be a light element configured to emit light of a color corresponding to the active strut. Secondary housing 1330 may include a coupling component 1302*b* operative to couple secondary housing 1330 to a strut of a bone alignment device. Secondary housing 1330 may be communicatively coupled to main body 1310 via communication element 1322, for example, forming a wired connection. In some embodiments, at least a portion of the hardware and/or software for operating adjustment compliance device 1304 may be arranged within secondary housing 1330.

Figure 14:
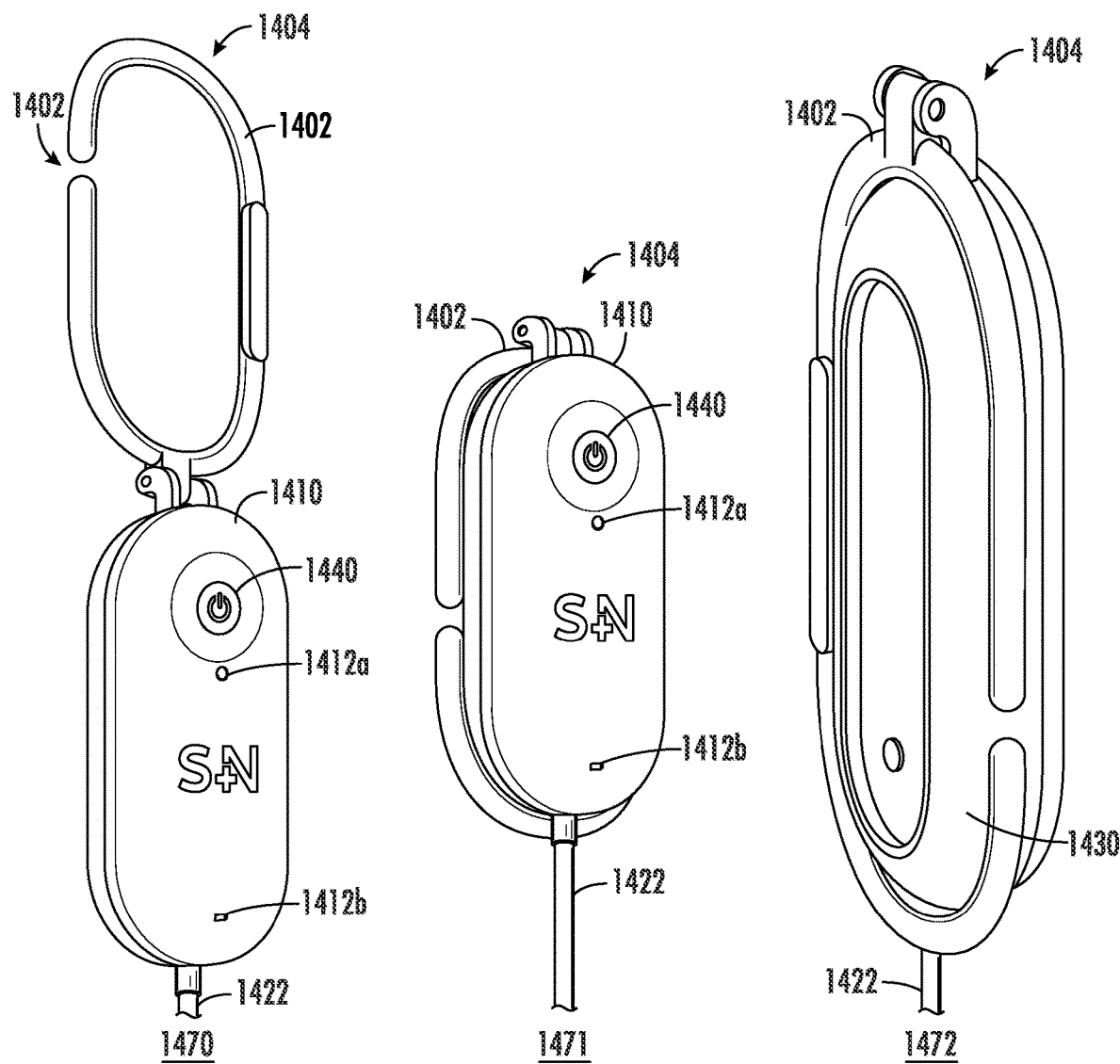
FIG. 14 illustrates an eighth embodiment of an adjustment compliance device.

FIG. 14 illustrates an eighth embodiment of an adjustment compliance device. As shown in FIG. 14, therein is depicted a front open view 1470, front closed view 1471, and back closed view 1472 of an adjustment compliance device 1404. In some embodiments, adjustment compliance device 1404 may include a power button 1440 and indicator elements 1412*a*, 1412*b*. Indicator element 1412*a* may operate to indicate an active component, such as the next strut to be adjusted for a bone alignment device. For example, indicator element 1412*a* may be a light element configured to emit light of a color corresponding to the active strut. Indicator element 1412*b* may be a power status indicator, for example, to indicate a level of charge of adjustment compliance device 1404.

Adjustment compliance device 1404 may include coupling component 1402 in the form of a hook or open loop configured to hang or otherwise support adjustment compliance device 1404 from a portion of a bone alignment device, such as a frame portion. In some embodiments, coupling component 1402 may be flexible to allow an opening to be expanded to fit around a portion of a bone alignment device, such as a frame portion, then return to an original position. As shown in views 1471 and 1472, coupling component 1402 may be moved to a closed position when not in use.

Figure 15A:
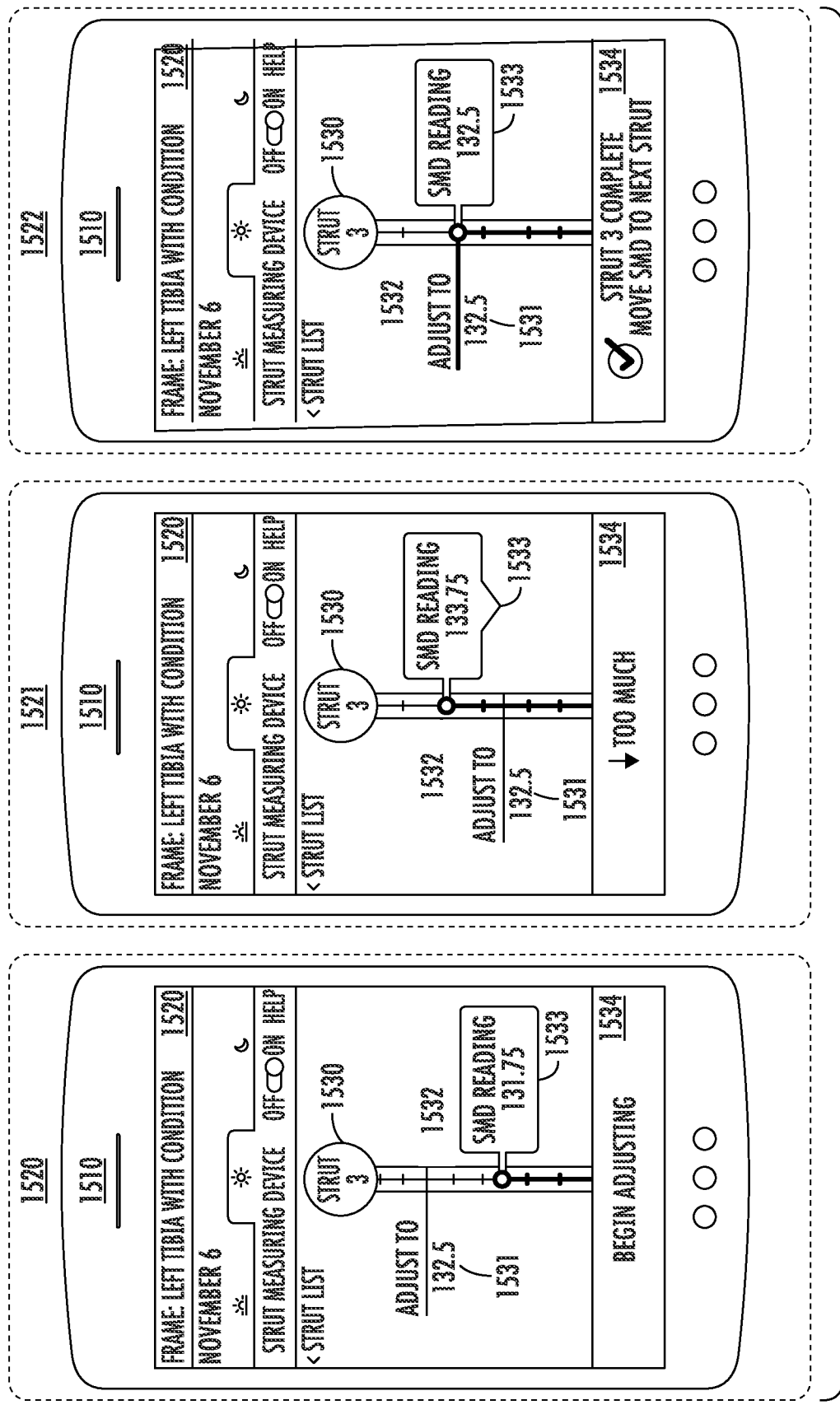

FIGS. 15A and 15B illustrate a computing device depicting embodiments of an external fixator adjustment screen. As shown in FIG. 15A, a user device 1510 may present an adjustment screen 1520 for automatically adjusting a strut using a measurement and feedback device 116 and/or an automatic adjustment device 118. Adjustment screen 1520 may present an active strut 1530, adjustment information 1532, an adjustment status 1534, and/or a graphical representation of the strut (for example, depicting markings on the strut for position information). In some embodiments, adjustment information 1532 may include an adjustment value 1531 (i.e., a length to adjust strut) and a current value 1533 (i.e., current length of strut). In state 1520, adjustment of strut 3 has begun and the length of strut 3 1533 needs to be lengthened to meet the adjustment value 1531. In state 1521, strut 3 has been over-lengthened, causing a "too much" status 1534 and indicators depicting that the length of strut 3 needs to be reduced. In state 1522, strut 3 has been adjusted to meet adjustment value 1531 and a "strut 3 complete" message is presented in status 1534.

Referring to FIG. 15B, in state 1523, adjustment screen 1520 may present a next strut to be adjusted, which, in FIG. 15B, has been adjusted to meet adjustment value 1531. In state 1524, all struts have been adjusted for the adjustment event for the prescription (for instance, a daily adjustment) and a complete status screen 1540 may be presented via user device 1510.

Figure 16C:
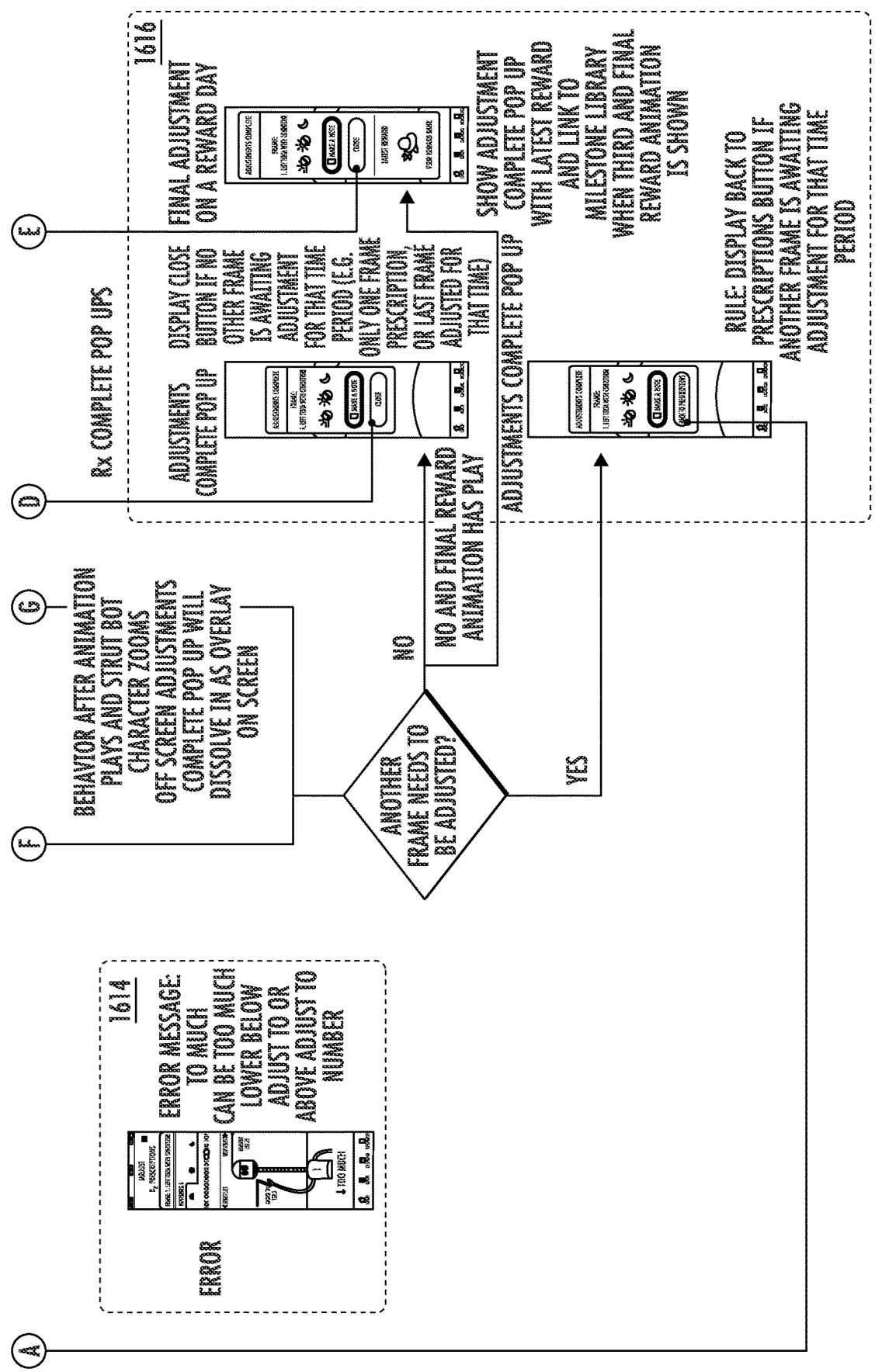

FIGS. 16A-16C illustrate embodiments of screens of an external fixator adjustment application. In general, FIGS. 16A-16C depict illustrative screens for a pediatric patient version of an external fixator adjustment application configured to present animations, GUI objects, rewards, incentives, and/or other elements to provide a positive user experience for pediatric patients and their caregivers. As shown in FIG. 16A, an external fixator adjustment application may include home screens 1602 that may be presented when the external fixator adjustment application is launched on a user device. From home screens 1602, a user may navigate to rewards screens 1604 and/or access a prescription screen 1606. From the prescription screen 1606, a user may launch manual prescription screens 1608, for example, for manually adjusting struts of a bone alignment device.

Referring to FIG. 16B, therein are depicted automatic adjustment screens 1610, for example, for implementing a prescription using a measurement and feedback device 116 and/or an automatic adjustment device 118. Completion animation screens 1612 may be presented for completion of a strut adjustment and/or a prescription for manual and/or automatic adjustment methods. Referring to FIG. 16C, an error screen 1614 may be presented responsive to detection of one or more error conditions, such as over adjustment of a strut, loss of communication between a user device and an adjustment compliance device, measurement and feedback device, and/or automatic adjustment device. One or more prescription completion screens 1616 may be presented responsive to a determination that a patient has completed a prescription.

FIG. 17 illustrates embodiments of an external fixator adjustment incentive screens. In some embodiments, an external fixator adjustment application may provide certain incentives, rewards, or other behavior-based information in order to enhance user experience and/or to promote proper prescription adherence. FIG. 17 depicts screens 1620-1623 depicting various behavior-based or incentive-based information for promoting prescription adherence by a user of external fixator adjustment application.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 18:
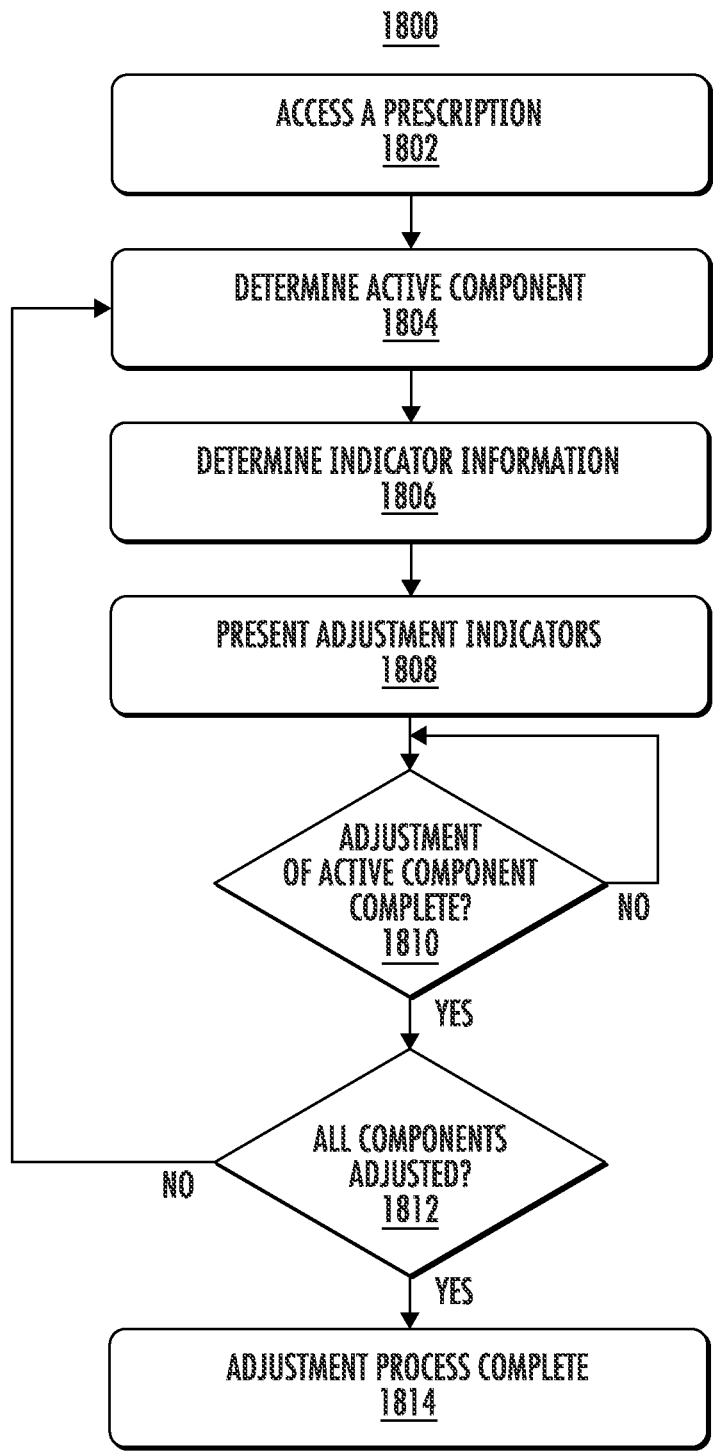
FIG. 18 illustrates a logic flow in accordance with the present disclosure.

FIG. 18 illustrates an embodiment of a logic flow 1800. Logic flow 1800 may be representative of some or all of the operations executed by one or more embodiments described herein. In some embodiments, logic flow 1800 may be representative of some or all of the operations of an adjustment process according to some embodiments.

At block 1802, logic flow 1800 may access a prescription. For example, computing device 110 may access prescription information 142 that may specify a prescription for adjusting struts of a bone alignment device. Logic flow 1800 may determine an active component at block 1804. For example, adjustment application 148 may determine the next strut to be adjusted according to the prescription. At block 1806, logic flow 1800 may determine indicator information. For example, adjustment application 148 may determine adjustment information 146 associated with adjusting the active strut, such as a color, number, or other designator associated with the active strut and/or a direction to adjust strut (e.g., lengthen/shorten, clockwise/counterclockwise rotation, and/or the like).

Logic flow 1800 may present adjustment indicators at block 1808. For example, adjustment application 148 may provide information, instructions, and/or the like to adjustment compliance device 104 to activate one or more indicators 112a-n to signal adjustment information to a user. For instance, if strut 1 is active, then adjustment compliance device 104 may activate indicator 112a to emit light in a color corresponding to a color band of strut 1. In another instance, if strut 1 is required to be rotated clockwise, for instance, to lengthen strut 1, then adjustment compliance device 104 may activate indicator 112n to indicate clockwise rotation of strut 1. A user may couple adjustment compliance device 104 (and/or measurement and feedback device 116 and/or an automatic adjustment device 118) to the strut indicated by indicator 112a, for example, to assure that the correct strut is being adjusted.

At block 1810, logic flow 1800 may determine whether adjustment of the active component is complete. In a manual adjustment process, a determination that adjustment of the active component is complete may be based on selection of a completion object on a screen (see, for example, FIG. 3) indicating that a user has completed adjustment of the active strut. In an automated or measurement/feedback-based adjustment process, a determination that adjustment of the active component is complete may be based on feedback from measurement and feedback device 116 and/or an automatic adjustment device 118 (see, for example, FIGS.

15A and 15B). If adjustment of the active component is complete, logic flow 1800 may determine whether all components have been adjusted at block 1812. If additional components require adjustments, logic flow 1800 may determine the active component at block 1804. If all components have been adjusted, logic flow 1800 may determine that the adjustment process is complete at block 1814.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

What is claimed is:

1. An adjustment compliance device for coupling to an external fixator including a plurality of adjustable length struts, each adjustable length strut including a color-coded identification band, each color-coded identification band including a unique color, the adjustable compliance device comprising:
    a main body having a coupling element to couple the adjustment compliance device to a portion of the adjustable medical apparatus;
    a communication interface for communicatively coupling the adjustment compliance device to an external computing device;
    a logic device configured to receive indicator information from the external computing device; and
    at least one light element arranged on the main body, the logic device to control the at least one light element based on the indicator information to emit a color corresponding to one of the unique colors of the color-coded identification band associated with one of the adjustable length struts to indicate which adjustable length strut to couple the adjustable compliance device to.

2. The adjustment compliance device of claim 1, wherein the coupling element comprises at least one of a clip to releasably clip the adjustment compliance device to a strut of the external fixator or a hook to hang the adjustment compliance device from a frame of the external fixator.

3. A method for facilitating compliance with an external fixator including a plurality of adjustable length struts, each adjustable length strut including a color-coded identification band, each color-coded identification band including a unique color, the method comprising:
    communicatively coupling an adjustment compliance device to a computing device;
    generating indicator information via the computing device based on an adjustment prescription;
    transmitting, via the computing device, the indicator information to the adjustment compliance device; and
    illuminating at least one light element on the adjustment compliance device with a unique color corresponding to one of the unique colors associated with one of the plurality of adjustable length struts to indicate which one of the plurality of adjustable length struts to couple the adjustment compliance device to.

* * * * *